(12) United States Patent
Casey et al.

(10) Patent No.: US 12,376,907 B2
(45) Date of Patent: Aug. 5, 2025

(54) PATIENT-SPECIFIC MEDICAL SYSTEMS, DEVICES, AND METHODS

(71) Applicant: Carlsmed, Inc., Carlsbad, CA (US)

(72) Inventors: Niall Patrick Casey, Carlsbad, CA (US); Michael J. Cordonnier, Carlsbad, CA (US); Justin Esterberg, Mercer Island, WA (US); Jeffrey Roh, Seattle, WA (US)

(73) Assignee: CARLSMED, INC., Carlsbad, CA (US)

( * ) Notice: Subject to any disclaimer, the term of this patent is extended or adjusted under 35 U.S.C. 154(b) by 0 days.

(21) Appl. No.: 18/983,335

(22) Filed: Dec. 16, 2024

(65) Prior Publication Data

US 2025/0114145 A1 Apr. 10, 2025

Related U.S. Application Data

(63) Continuation of application No. 18/783,369, filed on Jul. 24, 2024, which is a continuation of application
(Continued)

(51) Int. Cl.
*A61B 34/10* (2016.01)
*A61B 34/30* (2016.01)
(Continued)

(52) U.S. Cl.
CPC .............. *A61B 34/10* (2016.02); *A61B 34/30* (2016.02); *A61F 2/44* (2013.01); *G06N 20/00* (2019.01);
(Continued)

(58) Field of Classification Search
CPC ... A61B 34/10; A61B 34/30; A61B 2034/102; A61B 2034/105; A61B 2034/108;
(Continued)

(56) References Cited

U.S. PATENT DOCUMENTS

| 4,704,686 A | 11/1987 | Aldinger |
| 4,936,862 A | 6/1990 | Walker et al. |

(Continued)

FOREIGN PATENT DOCUMENTS

| CN | 104318009 A | 1/2015 |
| CN | 104353121 A | 2/2015 |

(Continued)

OTHER PUBLICATIONS

Georgiakakis et al., "Artificial intelligence in planned orthopaedic care", Sicot J. 2024;10:49, Nov. 21, 2024, pp. 1-8. (Year: 2024).*
(Continued)

*Primary Examiner* — Nay A Maung
*Assistant Examiner* — Jose M Torres
(74) *Attorney, Agent, or Firm* — Perkins Coie LLP

(57) ABSTRACT

Systems and methods for designing and implementing patient-specific surgical procedures and/or medical devices are disclosed. In some embodiments, a method includes receiving a patient data set of a patient. The patient data set is compared to a plurality of reference patient data sets, wherein each of the plurality of reference patient data sets is associated with a corresponding reference patient. A subset of the plurality of reference patient data sets is selected based, at least partly, on similarity to the patient data set and treatment outcome of the corresponding reference patient. Based on the selected subset, at least one surgical procedure or medical device design for treating the patient is generated.

28 Claims, 18 Drawing Sheets

Related U.S. Application Data

No. 18/139,907, filed on Apr. 26, 2023, now Pat. No. 12,137,983, which is a continuation of application No. 17/838,727, filed on Jun. 13, 2022, now Pat. No. 11,678,938, which is a continuation of application No. 17/342,439, filed on Jun. 8, 2021, now Pat. No. 11,376,076, which is a continuation of application No. PCT/US2021/012065, filed on Jan. 4, 2021, which is a continuation-in-part of application No. 17/124,822, filed on Dec. 17, 2020, now Pat. No. 11,854,683, and a continuation-in-part of application No. 16/735,222, filed on Jan. 6, 2020, now Pat. No. 10,902,944.

(51) Int. Cl.

| | | |
|---|---|---|
| *A61F 2/44* | (2006.01) | |
| *G06N 20/00* | (2019.01) | |
| *G06T 7/00* | (2017.01) | |
| *G16H 50/20* | (2018.01) | |
| *G16H 50/30* | (2018.01) | |
| *G16H 50/50* | (2018.01) | |

(52) U.S. Cl.
CPC ........... *G06T 7/0012* (2013.01); *G16H 50/20* (2018.01); *G16H 50/30* (2018.01); *G16H 50/50* (2018.01); *A61B 2034/102* (2016.02); *A61B 2034/105* (2016.02); *A61B 2034/108* (2016.02); *G06T 2207/20081* (2013.01); *G06T 2207/20084* (2013.01); *G06T 2207/30012* (2013.01)

(58) Field of Classification Search
CPC ...... A61F 2/44; A61F 2/30942; A61F 2/4455; A61F 2/446; A61F 2/447; A61F 2002/30593; A61F 2002/30962; A61F 2002/30985; A61F 2002/4632; G06N 20/00; G06T 7/0012; G06T 2207/20081; G06T 2207/20084; G06T 2207/30012; G16H 50/20; G16H 50/30; G16H 50/50; B33Y 80/00

See application file for complete search history.

(56) References Cited

U.S. PATENT DOCUMENTS

| | | |
|---|---|---|
| 5,431,562 A | 7/1995 | Andreiko et al. |
| D420,995 S | 2/2000 | Imamura |
| D436,580 S | 1/2001 | Navano |
| 6,315,553 B1 | 11/2001 | Sachdeva |
| 6,540,512 B1 | 4/2003 | Sachdeva |
| 6,696,073 B2 | 2/2004 | Boyce et al. |
| 6,772,026 B2 | 8/2004 | Bradbury |
| 6,932,842 B1 | 8/2005 | Litschko et al. |
| 6,978,188 B1 | 12/2005 | Christensen |
| 6,988,241 B1 | 1/2006 | Guttman |
| 7,174,282 B2 | 2/2007 | Hollister et al. |
| 7,187,790 B2 | 3/2007 | Sabol et al. |
| D548,242 S | 8/2007 | Viegers |
| D614,191 S | 4/2010 | Takano |
| 7,747,305 B2 | 6/2010 | Dean et al. |
| 7,756,314 B2 | 7/2010 | Karau et al. |
| 7,799,077 B2 | 9/2010 | Lang |
| D633,514 S | 3/2011 | Tokunaga |
| D656,153 S | 3/2012 | Imamura |
| 8,214,016 B2 | 7/2012 | Lavallee |
| 8,246,680 B2 | 8/2012 | Betz |
| 8,265,949 B2 | 9/2012 | Haddad |
| 8,275,594 B2 | 9/2012 | Lin |
| 8,337,507 B2 | 12/2012 | Lang |
| 8,343,221 B2 | 1/2013 | Trieu |
| 8,394,142 B2 | 3/2013 | Bertagnoli |
| 8,457,930 B2 | 6/2013 | Shroeder |
| 8,532,806 B1 | 9/2013 | Masson |
| 8,556,983 B2 | 10/2013 | Bojarski et al. |
| 8,644,568 B1 | 2/2014 | Hoffman |
| 8,735,773 B2 | 5/2014 | Lang |
| 8,758,357 B2 | 6/2014 | Frey |
| 8,775,133 B2 | 7/2014 | Schroeder |
| 8,781,557 B2 | 7/2014 | Dean |
| 8,843,229 B2 | 9/2014 | Vanasse |
| 8,855,389 B1 | 10/2014 | Hoffman |
| 8,870,889 B2 | 10/2014 | Frey |
| 9,020,788 B2 | 4/2015 | Lang |
| D735,231 S | 7/2015 | Omiya |
| D737,309 S | 8/2015 | Kito |
| 9,198,678 B2 | 12/2015 | Frey et al. |
| 9,208,558 B2 | 12/2015 | Dean |
| D757,025 S | 5/2016 | Kim |
| D761,842 S | 7/2016 | Johnson |
| 9,411,939 B2 | 8/2016 | Furrer |
| 9,445,907 B2 | 9/2016 | Meridew |
| 9,452,050 B2 | 9/2016 | Miles et al. |
| D774,076 S | 12/2016 | Fuller |
| 9,542,525 B2 | 1/2017 | Arisoy et al. |
| 9,642,633 B2 | 5/2017 | Frey et al. |
| 9,693,831 B2 | 7/2017 | Mosnier et al. |
| 9,707,058 B2 | 7/2017 | Bassett |
| 9,715,563 B1 | 7/2017 | Schroeder |
| D797,760 S | 9/2017 | Tsujimura |
| D797,766 S | 9/2017 | Ibsies |
| D798,312 S | 9/2017 | Tsujimura |
| 9,757,245 B2 | 9/2017 | O'Neil et al. |
| D798,894 S | 10/2017 | Ibsies |
| 9,775,680 B2 | 10/2017 | Bojarski et al. |
| 9,782,228 B2 | 10/2017 | Mosnier et al. |
| D812,628 S | 3/2018 | Okado |
| 9,993,341 B2 | 6/2018 | Vanasse |
| 10,034,676 B2 | 7/2018 | Donner |
| D825,605 S | 8/2018 | Jann |
| D826,977 S | 8/2018 | Nakajima |
| 10,089,413 B2 | 10/2018 | Wirx-Speetjens et al. |
| D841,675 S | 2/2019 | Hoffman |
| 10,213,311 B2 | 2/2019 | Mafhouz |
| D845,973 S | 4/2019 | Jaycobs |
| D845,974 S | 4/2019 | Cooperman |
| D847,165 S | 4/2019 | Kolbenheyer |
| D848,468 S | 5/2019 | Ng |
| D849,029 S | 5/2019 | Cooperman |
| D849,773 S | 5/2019 | Jiang |
| 10,292,770 B2 | 5/2019 | Ryan |
| 10,299,863 B2 | 5/2019 | Grbic et al. |
| D854,560 S | 7/2019 | Field |
| D854,561 S | 7/2019 | Field |
| 10,390,958 B2 | 8/2019 | Maclennan |
| D860,237 S | 9/2019 | Li |
| D860,238 S | 9/2019 | Bhardwaj |
| D866,577 S | 11/2019 | Eisert |
| D867,379 S | 11/2019 | Ang |
| D867,389 S | 11/2019 | Jamison |
| 10,463,433 B2 | 11/2019 | Turner et al. |
| D870,762 S | 12/2019 | Mendoza |
| 10,512,546 B2 | 12/2019 | Kamer et al. |
| 10,517,681 B2 | 12/2019 | Roh et al. |
| D872,117 S | 1/2020 | Kobayashi |
| D872,756 S | 1/2020 | Howell |
| D874,490 S | 2/2020 | Dodsworth |
| D875,761 S | 2/2020 | Heffernan |
| D876,454 S | 2/2020 | Knowles |
| D876,462 S | 2/2020 | Li |
| D877,167 S | 3/2020 | Knowles |
| D879,112 S | 3/2020 | Hejazi |
| 10,588,589 B2 | 3/2020 | Bregman-Amitai et al. |
| 10,603,055 B2 | 3/2020 | Donner et al. |
| D880,513 S | 4/2020 | Wang |
| D881,908 S | 4/2020 | Sunil |
| D881,910 S | 4/2020 | Lin |
| 10,621,289 B2 | 4/2020 | Schroeder |
| 10,631,988 B2 | 4/2020 | Arnold et al. |
| D884,008 S | 5/2020 | Thornberg |
| 10,646,236 B2 | 5/2020 | Donner et al. |

(56) References Cited

U.S. PATENT DOCUMENTS

| | | |
|---|---|---|
| 10,646,258 B2 | 5/2020 | Donner et al. |
| 10,736,698 B2 | 8/2020 | Bohl |
| 10,751,188 B2 | 8/2020 | Guo et al. |
| D896,825 S | 9/2020 | Abel |
| D896,828 S | 9/2020 | Linares |
| D898,054 S | 10/2020 | Everhart |
| D899,438 S | 10/2020 | Crafts |
| 10,806,597 B2 | 10/2020 | Sournac et al. |
| 10,902,944 B1 | 1/2021 | Casey et al. |
| D916,868 S | 4/2021 | Evangeliou |
| D916,879 S | 4/2021 | Mitsumori |
| D918,253 S | 5/2021 | Choe |
| 11,000,334 B1 | 5/2021 | Young |
| D921,675 S | 6/2021 | Kmak |
| D921,677 S | 6/2021 | Kmak |
| D921,687 S | 6/2021 | Kmak |
| D924,909 S | 7/2021 | Nasu |
| D925,567 S | 7/2021 | Hayamizu |
| D927,528 S | 8/2021 | Heisler |
| 11,083,586 B2 | 8/2021 | Cordonnier |
| 11,112,770 B2 | 9/2021 | Roh et al. |
| D933,692 S | 10/2021 | Smith |
| 11,166,764 B2 | 11/2021 | Roh et al. |
| 11,185,369 B2 | 11/2021 | Ryan |
| D937,870 S | 12/2021 | Pinto |
| D937,876 S | 12/2021 | Harvey |
| D938,461 S | 12/2021 | Hoffman |
| D938,986 S | 12/2021 | Grossberg |
| D940,178 S | 1/2022 | Ang |
| D946,022 S | 3/2022 | Nuttbrown |
| D946,023 S | 3/2022 | Nuttbrown |
| D946,024 S | 3/2022 | Vogler-Ivashchanka |
| D946,616 S | 3/2022 | Tsai |
| 11,278,413 B1 | 3/2022 | Lang |
| D958,151 S | 7/2022 | Casey et al. |
| 11,376,076 B2 | 7/2022 | Casey et al. |
| 11,432,943 B2 | 9/2022 | Casey et al. |
| 11,439,514 B2 | 9/2022 | Casey et al. |
| 11,443,838 B1 | 9/2022 | Cordonnier |
| 11,497,559 B1 | 11/2022 | Roh et al. |
| 11,678,938 B2 | 6/2023 | Casey et al. |
| 11,696,833 B2 | 7/2023 | Casey et al. |
| 11,717,412 B2 | 8/2023 | Casey et al. |
| 11,793,577 B1 | 10/2023 | Casey et al. |
| 11,806,241 B1 | 11/2023 | Hussain |
| 11,857,264 B2 | 1/2024 | Roh et al. |
| 12,133,803 B2 | 11/2024 | Casey et al. |
| 12,137,983 B2 | 11/2024 | Casey et al. |
| 2004/0104512 A1 | 6/2004 | Eidenschink |
| 2005/0234555 A1 | 10/2005 | Sutton et al. |
| 2005/0273170 A1 | 12/2005 | Navarro et al. |
| 2005/0277934 A1 | 12/2005 | Vardiman |
| 2007/0272747 A1 | 11/2007 | Woods et al. |
| 2007/0276369 A1 | 11/2007 | Allard et al. |
| 2007/0276501 A1 | 11/2007 | Betz |
| 2008/0227047 A1 | 9/2008 | Lowe |
| 2008/0294265 A1 | 11/2008 | Warkentine et al. |
| 2009/0062739 A1 | 3/2009 | Anderson |
| 2010/0100011 A1 | 4/2010 | Roche |
| 2010/0191088 A1 | 7/2010 | Anderson et al. |
| 2010/0217270 A1* | 8/2010 | Polinski ............ A61F 2/30942 700/98 |
| 2010/0217336 A1 | 8/2010 | Crawford et al. |
| 2010/0324692 A1 | 12/2010 | Uthgenannt |
| 2011/0196451 A1 | 8/2011 | Hill |
| 2011/0269104 A1 | 11/2011 | Berckmans |
| 2012/0150243 A9 | 6/2012 | Crawford et al. |
| 2012/0179258 A1 | 7/2012 | Glazer et al. |
| 2012/0296433 A1 | 11/2012 | Farin |
| 2012/0310364 A1 | 12/2012 | Li et al. |
| 2012/0322018 A1 | 12/2012 | Lowe |
| 2013/0323669 A1 | 12/2013 | Lowe |
| 2014/0072608 A1 | 3/2014 | Karagkiozaki |
| 2014/0074438 A1 | 3/2014 | Furrer |
| 2014/0081659 A1 | 3/2014 | Nawana et al. |
| 2014/0086780 A1 | 3/2014 | Miller |
| 2014/0100886 A1 | 4/2014 | Woods |
| 2014/0135940 A1 | 5/2014 | Goldstein |
| 2014/0164022 A1 | 6/2014 | Reed |
| 2014/0263674 A1 | 9/2014 | Cerveny |
| 2014/0272881 A1 | 9/2014 | Barsoum |
| 2014/0277487 A1 | 9/2014 | Davenport et al. |
| 2014/0350614 A1 | 11/2014 | Frey |
| 2015/0079533 A1 | 3/2015 | Lowe |
| 2015/0089590 A1 | 3/2015 | Krishnan et al. |
| 2015/0105891 A1 | 4/2015 | Golway et al. |
| 2015/0199488 A1 | 7/2015 | Falchuk |
| 2015/0213225 A1 | 7/2015 | Amarasingham |
| 2015/0324490 A1 | 11/2015 | Page |
| 2015/0328004 A1 | 11/2015 | Mafhouz |
| 2015/0332018 A1 | 11/2015 | Rosen |
| 2016/0001039 A1 | 1/2016 | Armour et al. |
| 2016/0012753 A1 | 1/2016 | Mehdian |
| 2016/0015465 A1 | 1/2016 | Steines et al. |
| 2016/0030067 A1 | 2/2016 | Frey et al. |
| 2016/0074048 A1 | 3/2016 | Pavlovskaia |
| 2016/0081810 A1 | 3/2016 | Reiley et al. |
| 2016/0117817 A1 | 4/2016 | Seel |
| 2016/0143744 A1 | 5/2016 | Bojarski et al. |
| 2016/0184054 A1 | 6/2016 | Lowe |
| 2016/0191887 A1 | 6/2016 | Casas |
| 2016/0210374 A1 | 7/2016 | Mosnier et al. |
| 2016/0217268 A1 | 7/2016 | Otto |
| 2016/0242857 A1 | 8/2016 | Scholl |
| 2016/0300026 A1 | 10/2016 | Bogoni et al. |
| 2016/0354039 A1 | 12/2016 | Soto et al. |
| 2016/0354213 A1 | 12/2016 | Cowan |
| 2016/0361025 A1 | 12/2016 | Reicher |
| 2016/0378919 A1 | 12/2016 | McNutt et al. |
| 2017/0000566 A1 | 1/2017 | Gordon |
| 2017/0014169 A1 | 1/2017 | Dean |
| 2017/0020679 A1 | 1/2017 | Maclennan |
| 2017/0035514 A1 | 2/2017 | Fox et al. |
| 2017/0046486 A1 | 2/2017 | Cunningham |
| 2017/0061375 A1 | 3/2017 | Laster |
| 2017/0068792 A1 | 3/2017 | Reiner |
| 2017/0112548 A1 | 4/2017 | Alamin et al. |
| 2017/0135706 A1 | 5/2017 | Frey et al. |
| 2017/0143494 A1 | 5/2017 | Mahfouz |
| 2017/0143831 A1 | 5/2017 | Varanasi et al. |
| 2017/0196499 A1 | 7/2017 | Hunter |
| 2017/0216047 A1 | 8/2017 | Hawkes et al. |
| 2017/0220740 A1 | 8/2017 | D'Urso |
| 2017/0242107 A1 | 8/2017 | Dussan et al. |
| 2017/0252107 A1 | 9/2017 | Turner et al. |
| 2017/0258526 A1 | 9/2017 | Lang |
| 2017/0262595 A1 | 9/2017 | Vorhis |
| 2017/0340447 A1 | 11/2017 | Mahfouz |
| 2017/0354510 A1 | 12/2017 | O'Neil et al. |
| 2017/0360358 A1 | 12/2017 | Amiot |
| 2017/0367645 A1 | 12/2017 | Klinder |
| 2018/0008349 A1 | 1/2018 | Gillman |
| 2018/0113992 A1 | 4/2018 | Eltorai et al. |
| 2018/0116727 A1 | 5/2018 | Caldwell et al. |
| 2018/0168499 A1 | 6/2018 | Bergold |
| 2018/0168731 A1 | 6/2018 | Reid |
| 2018/0185075 A1 | 7/2018 | She |
| 2018/0233222 A1 | 8/2018 | Daley |
| 2018/0233225 A1 | 8/2018 | Experton |
| 2018/0247020 A1 | 8/2018 | Itu et al. |
| 2018/0250075 A1 | 9/2018 | Cho |
| 2018/0303552 A1 | 10/2018 | Ryan |
| 2018/0303616 A1 | 10/2018 | Bhattacharyya et al. |
| 2018/0308569 A1 | 10/2018 | Luellen |
| 2018/0325599 A1 | 11/2018 | Seo |
| 2018/0338841 A1 | 11/2018 | Miller et al. |
| 2018/0360609 A1 | 12/2018 | Steines et al. |
| 2019/0039286 A1 | 2/2019 | Tempco et al. |
| 2019/0065685 A1 | 2/2019 | Pickover |
| 2019/0069956 A1 | 3/2019 | Ryan et al. |
| 2019/0088371 A1 | 3/2019 | Casey et al. |
| 2019/0099221 A1 | 4/2019 | Schmidt et al. |
| 2019/0201106 A1 | 7/2019 | Siemionow |
| 2019/0209731 A1 | 7/2019 | Keyak et al. |

(56) References Cited

U.S. PATENT DOCUMENTS

| | | |
|---|---|---|
| 2019/0262084 A1 | 8/2019 | Roh et al. |
| 2019/0266597 A1 | 8/2019 | Mohtar |
| 2019/0321132 A1 | 10/2019 | Weir |
| 2019/0328929 A1 | 10/2019 | Kugler et al. |
| 2019/0333622 A1 | 10/2019 | Levin |
| 2019/0350720 A1 | 11/2019 | Koffler et al. |
| 2019/0354693 A1 | 11/2019 | Yoon |
| 2019/0380782 A1 | 12/2019 | McAfee et al. |
| 2019/0380792 A1 | 12/2019 | Poltaretskyi et al. |
| 2019/0388131 A1 | 12/2019 | Mehl et al. |
| 2020/0021570 A1 | 1/2020 | Lin |
| 2020/0085509 A1 | 3/2020 | Roh et al. |
| 2020/0188130 A1 | 6/2020 | Jebsen et al. |
| 2020/0258605 A1 | 8/2020 | Blechman |
| 2020/0261156 A1 | 8/2020 | Schmidt |
| 2020/0289288 A1 | 9/2020 | Müller et al. |
| 2020/0315708 A1 | 10/2020 | Mosnier et al. |
| 2021/0059822 A1 | 3/2021 | Casey et al. |
| 2021/0064605 A1 | 3/2021 | Balint |
| 2021/0145519 A1 | 5/2021 | Mosnier et al. |
| 2021/0169576 A1 | 6/2021 | Ryan et al. |
| 2021/0192759 A1 | 6/2021 | Lang |
| 2021/0210189 A1 | 7/2021 | Casey et al. |
| 2021/0257094 A1 | 8/2021 | Takemoto et al. |
| 2021/0287770 A1 | 9/2021 | Anderson |
| 2021/0290319 A1 | 9/2021 | Poltaretskyi et al. |
| 2021/0315706 A1 | 10/2021 | Noshchenko et al. |
| 2021/0378752 A1* | 12/2021 | Paul ............. A61B 34/20 |
| 2021/0382457 A1 | 12/2021 | Roh et al. |
| 2022/0000625 A1 | 1/2022 | Cordonnier |
| 2022/0006642 A1 | 1/2022 | Maj et al. |
| 2022/0013211 A1 | 1/2022 | Steinberg et al. |
| 2022/0039965 A1 | 2/2022 | Casey et al. |
| 2022/0047402 A1 | 2/2022 | Casey et al. |
| 2022/0110686 A1 | 4/2022 | Roh et al. |
| 2022/0160405 A1 | 5/2022 | Casey et al. |
| 2022/0160518 A1 | 5/2022 | Casey et al. |
| 2022/0387191 A1 | 12/2022 | Cordonnier |
| 2022/0401150 A1 | 12/2022 | Cordonnier |
| 2022/0409140 A1 | 12/2022 | Cordonnier |
| 2023/0014384 A1 | 1/2023 | Cordonnier |
| 2023/0023440 A1 | 1/2023 | Casey et al. |
| 2023/0034731 A1 | 2/2023 | Cordonnier |
| 2023/0052263 A1 | 2/2023 | Casey et al. |
| 2023/0067537 A1 | 3/2023 | Casey et al. |
| 2023/0086886 A1 | 3/2023 | Casey et al. |
| 2023/0136813 A1 | 5/2023 | Cordonnier |
| 2023/0138162 A1 | 5/2023 | Winston |
| 2023/0255690 A1* | 8/2023 | Castro ............. A61B 34/10 623/11.11 |
| 2023/0268040 A1 | 8/2023 | Cordonnier |
| 2024/0016614 A1 | 1/2024 | Casey et al. |
| 2024/0065767 A1 | 2/2024 | Cordonnier |
| 2024/0079114 A1 | 3/2024 | Casey et al. |
| 2024/0138919 A1 | 5/2024 | Casey et al. |
| 2024/0138921 A1 | 5/2024 | Roh et al. |
| 2024/0261029 A1 | 8/2024 | Casey et al. |
| 2024/0319709 A1 | 9/2024 | Roh et al. |
| 2024/0341960 A1 | 10/2024 | Casey |
| 2024/0374316 A1 | 11/2024 | Casey et al. |
| 2024/0374389 A1 | 11/2024 | Casey et al. |

FOREIGN PATENT DOCUMENTS

| | | |
|---|---|---|
| CN | 204468348 U | 7/2015 |
| CN | 105796214 A | 7/2016 |
| CN | 106202861 A | 12/2016 |
| CN | 107220933 A | 9/2017 |
| CN | 108670506 A | 10/2018 |
| CN | 110575289 A | 12/2019 |
| CN | 111281613 A | 6/2020 |
| CN | 112155792 A | 1/2021 |
| CN | 113643790 A | 11/2021 |
| EP | 3120796 A1 | 1/2017 |
| JP | 2011517996 A | 6/2011 |
| JP | 2012531265 A | 12/2012 |
| JP | 2016536051 A | 11/2016 |
| WO | 9507509 A1 | 3/1995 |
| WO | 2004110309 A2 | 12/2004 |
| WO | 2008027549 A2 | 3/2008 |
| WO | 2010151564 A1 | 12/2010 |
| WO | 2011080260 A1 | 7/2011 |
| WO | 2012154534 A1 | 11/2012 |
| WO | 2014145267 A1 | 9/2014 |
| WO | 2014180972 A2 | 11/2014 |
| WO | 2015075423 A2 | 5/2015 |
| WO | 2016102025 A1 | 6/2016 |
| WO | 2016172694 A1 | 10/2016 |
| WO | 2017116346 A1 | 7/2017 |
| WO | 2018193316 A2 | 10/2018 |
| WO | 2019112917 A1 | 6/2019 |
| WO | 2019148154 A1 | 8/2019 |
| WO | 2019165152 A1 | 8/2019 |
| WO | 2019241167 A1 | 12/2019 |
| WO | 2020055874 A1 | 3/2020 |
| WO | 2022045956 A1 | 3/2022 |
| WO | 2023034405 A1 | 3/2023 |

OTHER PUBLICATIONS

Farhadi et al., "Applications of artificial intelligence in orthopaedic surgery", Front Med Technol. Dec. 15, 2022;4:995526, pp. 1-14. (Year: 2022).*

Clement, R.C. et al., "A proposed set of metrics for standardized outcome reporting in the management of low back pain." Acta Orthopaedica. Sep. 3, 2015;86 (5); 523-33.

De Beer, N. et al., "Patient-specific intervertebral disc implants using rapid manufacturing technology." Rapid Prototyping Journal 19.2: 2013, 126-139.

Endo, Kenji et al. "Measurement of whole spine sagittal alignment using the Slot radiography of the Sonialvision safire series clinical application." Medical Now, No. 78; Aug. 2015, 4 pages.

Eshkalak, S.K. et al., "The role of three-dimensional printing in healthcare and medicine." Materials and Design 194, Jul. 10, 20202, 15 pages.

Examination Report for European Application No. 19859930.0, mailed Mar. 12, 2024, 5 pages.

Extended European Search Report for European Application No. 18885367.5, mailed Aug. 16, 2021, 8 pages.

Extended European Search Report for European Application No. 19859930.0, mailed Jun. 22, 2022, 7 pages.

Extended European Search Report for European Application No. 19890663.8, mailed Jul. 29, 2022, 8 pages.

Haglin, J.M. et al., "Patient-specific orthopaedic implants." Orthopaedic surgery 8.4: 2016, 417-424.

Hammoudeh J.A. et al., "Current Status of Surgical Planning for Orthognathic Surgery: Traditional Methods versus 3D Surgical Planning." PRS Global Open, Feb. 2015, 11 pages.

Harrysson, O. et al., "Custom-designed orthopedic implants evaluated using finite element analysis of patient-specific computed tomography data: femoral-component case study." BMC Musculoskeletal Disorders. Dec. 2007, 8:91, 10 pages.

Hartzler, A. et al., "Integrating Patient-Reported Outcomes into Spine Surgical Care through Visual Dashboards: Lessons Learned from Human-Centered Design." eGEMs. 2015;3(2), 20 pages.

International Search Report and Written Opinion for International Application No. PCT/US19/50885, mailed Jan. 28, 2020, 21 pages.

International Search Report and Written Opinion for International Application No. PCT/US19/63855, mailed Feb. 14, 2020, 15 pages.

International Search Report and Written Opinion for International Application No. PCT/US22/37640, mailed Nov. 15, 2022, 13 pages.

International Search Report and Written Opinion for International Patent Application No. PCT/US2018/063530, mailed Feb. 12, 2019, 16 pages.

International Search Report and Written Opinion for International Patent Application No. PCT/US21/12065, mailed Apr. 29, 2021, 19 pages.

(56) References Cited

OTHER PUBLICATIONS

Mangano C. et al., "Combining Intraoral Scans, Cone Beam Computed Tomography and Face Scans: The Virtual Patient." Journal of Craniofacial Surgery, Nov. 1, 2018:29(8): 27 pages.
Materialise Mimics, "Efficiently turn scans into accurate virtual 3D models," Retrieved on Nov. 1, 2019 at www. materialize.com/en/medical/software/mimics, 1 page.
Office Action for Japanese Application No. 2020-550591, mailed Dec. 26, 2022, 4 pages, English Translation.
Office Action for Japanese Application No. 2022-541805, mailed Jul. 25, 2024, 6 pages, English Translation.
Pimenta, Dr. Luiz, "Current Surgical Strategies to Restore Proper Sagittal Alignment," Journal of Spine 2015, vol. 4, Issue 4, 2 pages.
Pruthi, G. et al., "Comprehensive review of guidelines to practice prosthodontic and implant procedures during COVID-19 pandemic." Journal of Oral Biology and Craniofacial Research 10, Oct. 17, 2020, 8 pages.
Swennen, G.R.J. et al., "Three-Dimensional Treatment Planning of Orthognathic Surgery in the Era of Virtual Imaging." American Assoc. of Oral and Maxillofacial Surgeons 67:2080-2092, 2009.

\* cited by examiner

400

| PATIENT | |
|---|---|
| Pt. ID | JDoe |
| Metric | Value |
| Age | 58 |
| Gender | M |
| BMI | 32 |
| LL | 40 |
| PI | 55 |
| Levels | 4 |

*FIG. 4A*

| | Pt. ID | X123 | Pt. ID | Y456 | Pt. ID | Z789 | Pt. ID | A246 |
|---|---|---|---|---|---|---|---|---|
| | Metric | Value | Metric | Value | Metric | Value | Metric | Value |
| | Age | 56 | Age | 66 | Age | 63 | Age | 73 |
| | Gender | F | Gender | F | Gender | M | Gender | M |
| | BMI | 38 | BMI | 38 | BMI | 30 | BMI | 30 |
| Study Group X | LL | 36 | LL | 41 | LL | 39 | LL | 40 |
| | PI | 51 | PI | 52 | PI | 50 | PI | 48 |
| | Levels | 3 | Levels | 4 | Levels | 4 | Levels | 5 |
| | Outcome | | Outcome | | Outcome | | Outcome | |
| | Fused | Y | Fused | Y | Fused | Y | Fused | N |
| | HRQL | A | HRQL | B | HRQL | A | HRQL | D |
| | Complications | 0 | Complications | 0 | Complications | 1 | Complications | 0 |
| | Surg. Intervention | | Surg. Intervention | | Surg. Intervention | | Surg. Intervention | |
| | Imp. design | Stock | Imp. design | Stock | Imp. design | Stock | Imp. design | Stock |
| | Imp placemt | A | Imp placemt | A | Imp placemt | B | Imp placemt | B |
| | Surg. Appr. | Lat | Surg. Appr. | Ant | Surg. Appr. | Lat | Surg. Appr. | Post |

| | Pt. ID | B135 | Pt. ID | C468 | Pt. ID | D357 | Pt. ID | E468 |
|---|---|---|---|---|---|---|---|---|
| | Metric | Value | Metric | Value | Metric | Value | Metric | Value |
| | Age | 73 | Age | 60 | Age | 58 | Age | 78 |
| | Gender | F | Gender | M | Gender | M | Gender | M |
| | BMI | 37 | BMI | 32 | BMI | 29 | BMI | 30 |
| Practice Y | LL | 40 | LL | 40 | LL | 39 | LL | 40 |
| | PI | 55 | PI | 55 | PI | 52 | PI | 48 |
| | Levels | 4 | Levels | 4 | Levels | 4 | Levels | 3 |
| | Outcome | | Outcome | | Outcome | | Outcome | |
| | Fused | Y | Fused | Y | Fused | N | Fused | N |
| | HRQL | A | HRQL | A | HRQL | C | HRQL | F |
| | Complications | 0 | Complications | 0 | Complications | 1 | Complications | 0 |
| | Surg. Intervention | | Surg. Intervention | | Surg. Intervention | | Surg. Intervention | |
| | Imp. design | PS | Imp. design | PS | Imp. design | Stock | Imp. design | Stock |
| | Imp placemt | A | Imp placemt | A | Imp placemt | B | Imp placemt | B |
| | Surg. Appr. | Ant | Surg. Appr. | Ant, Lat | Surg. Appr. | Post | Surg. Appr. | Lat |

| | Pt. ID | F135 | Pt. ID | G468 | Pt. ID | H357 | Pt. ID | J468 |
|---|---|---|---|---|---|---|---|---|
| | Metric | Value | Metric | Value | Metric | Value | Metric | Value |
| | Age | 73 | Age | 60 | Age | 63 | Age | 71 |
| | Gender | F | Gender | M | Gender | M | Gender | M |
| | BMI | 33 | BMI | 42 | BMI | 31 | BMI | 30 |
| University Z | LL | 40 | LL | 40 | LL | 39 | LL | 40 |
| | PI | 55 | PI | 55 | PI | 52 | PI | 50 |
| | Levels | 4 | Levels | 4 | Levels | 4 | Levels | 3 |
| | Outcome | | Outcome | | Outcome | | Outcome | |
| | Fused | Y | Fused | Y | Fused | Y | Fused | N |
| | HRQL | A | HRQL | A | HRQL | A | HRQL | F |
| | Complications | 0 | Complications | 0 | Complications | 1 | Complications | 2 |
| | Surg. Intervention | | Surg. Intervention | | Surg. Intervention | | Surg. Intervention | |
| | Imp. design | PS | Imp. design | PS | Imp. design | PS | Imp. design | Stock |
| | Imp placemt | A | Imp placemt | A | Imp placemt | B | Imp placemt | B |
| | Surg. Appr. | Post | Surg. Appr. | Ant, Lat | Surg. Appr. | Ant, Lat | Surg. Appr. | Lat |

*FIG. 4B*

|  | Pre-op Similarity | | Outcome quotient |
| --- | --- | --- | --- |
|  | Pt. ID | Value |  |
| 410a → | X123 | 9 | 1 |
|  | Y456 | 18 | 2 |
|  | Z789 | 11 | 2 |
|  | A246 | 25 | 9 |
|  | B135 | 20 | 1 |
| 410b → | C468 | 2 | 1 |
| 410c → | D357 | 5 | 9 |
|  | E468 | 30 | 10 |
|  | F135 | 16 | 1 |
|  | G468 | 12 | 1 |
| 410d → | H357 | 8 | 2 |
|  | J468 | 21 | 12 |

420 (Pre-op Similarity); 430 (Outcome quotient)

New Surgery Plan

| Appointment Info |
|---|
| 📅 Surgery Date<br>Jan 8, 2021 |
| ✓ Surgery Date Status<br>Scheduled |
| 👤 Rep<br>Apple Rep User |
| 👤 Surgeon<br>Apple User |
| 👤 Patient ID<br>Hospital Patient ID |
| 👤 Gender<br>Female |
| 📅 Age<br>62 |
| 📷 Plan Image |

701 { (brackets around all Appointment Info rows)

New Surgery Plan

| Other Fields |
|---|
| ▫ Patient Name<br>Jane Doe |
| ▫ Patient MRN<br>MRN |
| ▫ Patient BMI<br>26 |
| ▫ Patient ODI<br>44 |
| ▫ Dexa (Normal, Osteopenia, Osteoporosis)<br>Normal |
| ▫ VAS-Back<br>56 |
| ▫ VAS-Leg |

701 { (Patient Name, Patient MRN, Patient BMI)
702 { (Patient ODI, Dexa, VAS-Back, VAS-Leg)

New Surgery Plan

| Other Fields |
|---|
| Normal |
| ▫ VAS-Back<br>56 |
| ▫ VAS-Leg<br>78 |
| ▫ Pre-operative Pelvic Incidence (PI)<br>67 |
| ▫ Pre-operative Lumbar Lorodisis (LL)<br>43 |
| ▫ Pre-operative PI-LL Angle<br>24 |
| ▫ Pre-operative Lumbar Coronal Cobb<br>7 |

702 { (all rows)

*FIG. 7C*

PATIENT-SPECIFIC MEDICAL SYSTEMS, DEVICES, AND METHODS

CROSS-REFERENCE TO RELATED APPLICATIONS

This application is a continuation of U.S. patent application Ser. No. 18/783,369, entitled "PATIENT-SPECIFIC MEDICAL SYSTEMS, DEVICES, AND METHODS," filed Jul. 24, 2024, which is a continuation of U.S. patent application Ser. No. 18/139,907 (now U.S. Pat. No. 12,137,983), entitled "PATIENT-SPECIFIC MEDICAL SYSTEMS, DEVICES, AND METHODS," filed Apr. 26, 2023, which is a continuation of U.S. patent application Ser. No. 17/838,727 (now U.S. Pat. No. 11,678,938), entitled "PATIENT-SPECIFIC MEDICAL SYSTEMS, DEVICES, AND METHODS," filed on Jun. 13, 2022, which is a continuation of U.S. patent application Ser. No. 17/342,439 (now U.S. Pat. No. 11,376,076) entitled "PATIENT-SPECIFIC MEDICAL SYSTEMS, DEVICES, AND METHODS," filed on Jun. 8, 2021, which is a continuation of International Application No. PCT/US21/12065, entitled "PATIENT-SPECIFIC MEDICAL PROCEDURES AND DEVICES, AND ASSOCIATED SYSTEMS AND METHODS," filed on Jan. 4, 2021, which is a continuation-in-part of U.S. patent application Ser. No. 17/124,822, filed on Dec. 17, 2020 (now U.S. Pat. No. 11,854,683), entitled "PATIENT-SPECIFIC MEDICAL PROCEDURES AND DEVICES, AND ASSOCIATED SYSTEMS AND METHODS," and is also a continuation-in-part of U.S. patent application Ser. No. 16/735,222 (now U.S. Pat. No. 10,902,944) entitled "PATIENT-SPECIFIC MEDICAL PROCEDURES AND DEVICES, AND ASSOCIATED SYSTEMS AND METHODS," filed on Jan. 6, 2020. All of these patents and applications are incorporated by reference herein in their entireties.

TECHNICAL FIELD

The present disclosure is generally related to designing and implementing medical care, and more particularly to systems and methods for designing and implementing surgical procedures and/or medical devices.

BACKGROUND

Numerous types of data associated with patient treatments and surgical interventions are available. To determine treatment protocols for a patient, physicians often rely on a subset of patient data available via the patient's medical record and historical outcome data. However, the amount of patient data and historical data may be limited, and the available data may not be correlated or relevant to the particular patient to be treated. Additionally, although digital data collection and processing power have improved, technologies using collected data to determine optimal treatment protocols have lagged. For example, conventional technologies in the field of orthopedics may lack the capability to draw upon large data sets to generate and optimize patient-specific treatments (e.g., surgical interventions and/or implant designs) to achieve favorable treatment outcomes.

BRIEF DESCRIPTION OF THE DRAWINGS

The accompanying drawings illustrate various embodiments of systems, methods, and embodiments of various other aspects of the disclosure. Any person with ordinary skill in the art will appreciate that the illustrated element boundaries (e.g., boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

FIGS. 4A-4C illustrate exemplary data sets that may be used and/or generated in connection with the methods described herein, according to an embodiment. FIG. 4A illustrates a patient data set. FIG. 4B illustrates a plurality of reference patient data sets. FIG. 4C illustrates similarity scores and outcome scores for the reference patient data sets of FIG. 4B.

FIGS. 7A-7D illustrates an exemplary patient data set that may be used and/or generated in connection with the methods described herein, according to an embodiment.

FIGS. 9A-1-9B-2 illustrate an exemplary virtual model of a patient's spine in a pre-operative anatomical configuration and a corrected anatomical configuration. More specifically, FIGS. 9A-1 and 9A-2 illustrates the pre-operative anatomical configuration of the patient, FIGS. 9B-1 and 9B-2 illustrates the corrected anatomical configuration.

DETAILED DESCRIPTION

Figure 1:
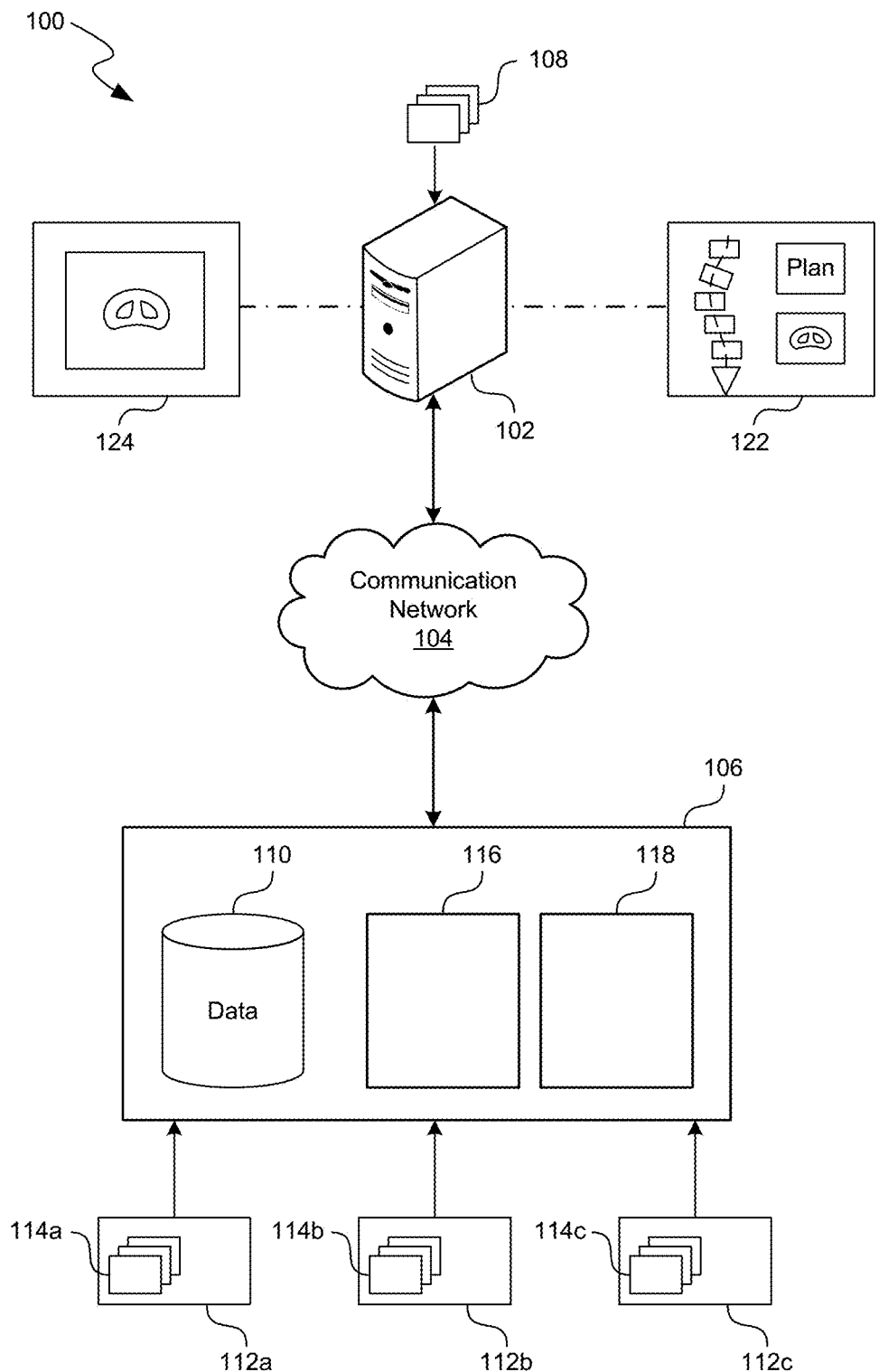
FIG. 1 is a network connection diagram illustrating a system for providing patient-specific medical care, according to an embodiment.

The present technology is directed to systems and methods for planning and implementing medical procedures and/or devices. For example, in many of the embodiments disclosed herein, a method of providing medical care includes comparing a patient data set of a patient to be treated with a plurality of reference patient data sets (e.g., data from previously-treated patients). The method can include selecting a subset of the reference patient data sets, e.g., based on similarity of the reference patient data set to the patient data set and/or whether the reference patient had a favorable treatment outcome. The selected subset can be used to generate a surgical procedure and/or medical device design that is likely to produce a favorable treatment outcome for the particular patient. In some embodiments, the selected subset is analyzed to identify correlations between patient pathology, surgical procedures, device designs, and/or treatment outcomes, and these correlations are used to determine a personalized treatment protocol with a higher likelihood of success.

In the context of orthopedic surgery, systems with improved computing capabilities (e.g., predictive analytics, machine learning, neural networks, artificial intelligence (AI)) can use large data sets to define improved or optimal surgical interventions and/or implant designs for a specific patient. The patient's entire data can be characterized and compared to aggregated data from groups of prior patients (e.g., parameters, metrics, pathologies, treatments, outcomes). In some embodiments, the systems described herein use this aggregated data to formulate potential treatment solutions (e.g., surgical plans and/or implant designs for spine and orthopedic procedures) and analyze the associated likelihood of success. These systems can further compare potential treatment solutions to determine an optimal patient-specific solution that is expected to maximize the likelihood for a successful outcome.

For example, if a patient presents with a spinal deformity pathology that can be described with data including lumbar lordosis, Cobb angles, coronal parameters (e.g., coronal balance, global coronal balance, coronal pelvic tilt, etc.), sagittal parameters (e.g., pelvic incidence, sacral slope, thoracic kyphosis, etc.) and/or pelvic parameters, an algorithm using these data points as inputs can be used to describe an optimal surgical plan and/or implant design to correct the subject pathology and improve the patient's outcome. As additional data inputs are used to describe the pathology (e.g., disc height, segment flexibility, bone quality, rotational displacement), the algorithm can use these additional inputs to further define an optimal surgical plan and/or implant design for that particular patient and their pathology.

In some embodiments, the present technology can automatically or at least semi-automatically determine a corrected anatomical configuration for a subject patient suffering from one or more deformities. For example, the computing systems described herein can apply mathematical rules for select parameters (e.g., lumbar lordosis, Cobb angles, etc.) and/or identify similar patients by analyzing reference patient data sets, and, based on the rules and/or comparison to other patients, can provide a recommended anatomical configuration that represents the optimal outcome if the subject patient were to undergo surgery. In some embodiments, the systems and methods described herein generate a virtual model of the corrected/recommended anatomical configuration (e.g., for surgeon review).

In some embodiments, the present technology can also automatically or at least semi-automatically generate a surgical plan for achieving a previously-identified corrected anatomical configuration for a subject patient. For example, based off the virtual model of the corrected anatomical configuration, the systems and methods herein can determine a type of surgery (e.g., spinal fusion surgery, non-fusion surgery, etc.), a surgical approach (e.g., anterior, posterior, etc.), and/or spinal parameters for the corrected anatomical configuration (e.g., lumbar lordosis, Cobb angles, etc.). The surgical plan can be transmitted to a surgeon for review and approval. In some embodiments, the present technology can also design one or more patient-specific implants for achieving the corrected anatomical configuration via the surgical plan.

In some embodiments, the present technology provides systems and methods that generate multiple anatomical models of the patient. For example, a first model may show the patient's native (e.g., pre-operative) anatomical configuration, and a second model may provide a simulation of the patient's corrected (e.g., post-operative) anatomical configuration. The second virtual model may optionally include one or more virtual implants shown as implanted at one or more target regions of the patient. Spine metrics (e.g., lumbar lordosis, Cobb angles, coronal parameters, sagittal parameters, pelvic parameters, etc.) can also be provided for both the pre-operative anatomical configuration and expected post-operative anatomical configuration.

In some embodiments, the present technology includes generating, designing, and/or providing patient-specific medical procedures for multiple locations within a patient. For example, the present technology can include identifying at least two target regions or sites within a patient (e.g., a first vertebral level and a second vertebral level) for surgical intervention. The present technology can then design at least two patient-specific implants for implantation at the at least two target regions. The at least two patient-specific implants can each be specifically designed for their respective target region, and thus can have different geometries. In some embodiments, the corrected anatomical configuration of the patient is only achieved by implanting each of the at least two patient-specific implants. In the context of spinal surgery, for example, the present technology may provide a first patient-specific interbody device to be implanted between the L2 and L3 vertebrae, a second patient-specific interbody device to be implanted between the L3 and L4 vertebrae, and a third patient-specific interbody device to be implanted between the L4 and L5 vertebrae.

In some embodiments, the present technology can predict, model, or simulate disease progression within a particular patient to aid in diagnosis and/or treatment planning. The simulation can be done to model and/or estimate future anatomical configurations and/or spine metrics of the patient (a) if no surgical intervention occurs, or (b) for a variety of different surgical intervention options. The progression modeling can thus be used to determine the optimal time for surgical intervention and/or to select which surgical intervention provides the best long-term outcomes. In some embodiments, the disease progression modelling is performed using one or more machine learning models trained based on a plurality of reference patients.

In a particular non-limiting example, the present technology includes a method for providing patient-specific medical care for a subject patient. The method can include receiving a patient-data set for the subject patient that includes one or more images of the patient's spinal region showing the patient's native anatomical configuration. The method can further include determining a corrected anatomical configuration for the subject patient that is different than the native anatomical configuration, and creating a virtual model of the corrected anatomical configuration. The method can further include generating surgical plan and designing one or more patient-specific implants for achieving the corrected anatomical configuration in the subject patient. In representative embodiments, the foregoing method can be performed by a system storing computer-executable instructions that, when executed, cause the system to perform the steps of method.

In a particular non-limiting example, the present technology includes a method for designing a patient-specific orthopedic implant for a subject patient. The method can include receiving a patient data set of the subject patient, the patient data set including spinal pathology data for the subject patient. The patient data set can be compared to a plurality of reference patient data sets to identify one or more similar patient data sets in the plurality of reference patient data sets, with each identified similar patient data set corresponding to a reference patient having similar spinal pathology to the subject patient and who received treatment with an orthopedic implant. The method can further include selecting a subset of the one or more similar patient data sets based on whether the similar patient data sets indicated the reference patient had a favorable outcome following implantation of their orthopedic implant. The method can further include identifying, for at least one similar reference patients of the selected subset, surgical procedure data and design data for the respective orthopedic implant that produced the favorable outcome in the similar reference patient. Based on the design data and the surgical produced data that produced the favorable outcome in the similar reference patient, the patient-specific orthopedic implant for the subject patient and a surgical procedure for implanting the patient-specific orthopedic implant into the subject patient can be designed. In some embodiments, the method can further include outputting fabrication instructions for causing a manufacturing system to manufacture the patient-specific orthopedic implant according to the generated design. In representative embodiments, the foregoing method can be performed by a system storing computer-executable instructions that, when executed, cause the system to perform the steps of method.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

As used herein and in the appended claims, the singular forms "a," "an," and "the" include plural references unless the context clearly dictates otherwise.

Although the disclosure herein primarily describes systems and methods for treatment planning in the context of orthopedic surgery, the technology may be applied equally to medical treatment and devices in other fields (e.g., other types of surgical practice). Additionally, although many embodiments herein describe systems and methods with respect to implanted devices, the technology may be applied equally to other types of medical devices (e.g., non-implanted devices).

FIG. 1 is a network connection diagram illustrating a computing system 100 for providing patient-specific medical care, according to an embodiment. As described in further detail herein, the system 100 is configured to generate a medical treatment plan for a patient. In some embodiments, the system 100 is configured to generate a medical treatment plan for a patient suffering from an orthopedic or spinal disease or disorder, such as trauma (e.g., fractures), cancer, deformity, degeneration, pain (e.g., back pain, leg pain), irregular spinal curvature (e.g., scoliosis, lordosis, kyphosis), irregular spinal displacement (e.g., spondylolisthesis, lateral displacement axial displacement), osteoarthritis, lumbar degenerative disc disease, cervical degenerative disc disease, lumbar spinal stenosis, or cervical spinal stenosis, or a combination thereof. The medical treatment plan can include surgical information, surgical plans, technology recommendations (e.g., device and/or instrument recommendations), and/or medical device designs. For example, the medical treatment plan can include at least one treatment procedure (e.g., a surgical procedure or intervention) and/or at least one medical device (e.g., an implanted medical device (also referred to herein as an "implant" or "implanted device") or implant delivery instrument).

In some embodiments, the system 100 generates a medical treatment plan that is customized for a particular patient or group of patients, also referred to herein as a "patient-specific" or "personalized" treatment plan. The patient-specific treatment plan can include at least one patient-specific surgical procedure and/or at least one patient-specific medical device that are designed and/or optimized for the patient's particular characteristics (e.g., condition, anatomy, pathology, condition, medical history). For example, the patient-specific medical device can be designed and manufactured specifically for the particular patient, rather than being an off-the-shelf device. However, it shall be appreciated that a patient-specific treatment plan can also include aspects that are not customized for the particular patient. For example, a patient-specific or personalized surgical procedure can include one or more instructions, portions, steps, etc. that are non-patient-specific. Likewise, a patient-specific or personalized medical device can include one or more components that are non-patient-specific, and/or can be used with an instrument or tool that is non-patient-specific. Personalized implant designs can be used to manufacture or select patient-specific technologies, including medical devices, instruments, and/or surgical kits. For example, a personalized surgical kit can include one or more patient-specific devices, patient-specific instruments, non-patient-specific technology (e.g., standard instruments, devices, etc.), instructions for use, patient-specific treatment plan information, or a combination thereof.

The system 100 includes a client computing device 102, which can be a user device, such as a smart phone, mobile device, laptop, desktop, personal computer, tablet, phablet, or other such devices known in the art. As discussed further herein, the client computing device 102 can include one or more processors, and memory storing instructions executable by the one or more processors to perform the methods described herein. The client computing device 102 can be associated with a healthcare provider that is treating the patient. Although FIG. 1 illustrates a single client computing device 102, in alternative embodiments, the client computing device 102 can instead be implemented as a client computing system encompassing a plurality of computing devices, such that the operations described herein with respect to the client computing device 102 can instead be performed by the computing system and/or the plurality of computing devices.

The client computing device 102 is configured to receive a patient data set 108 associated with a patient to be treated. The patient data set 108 can include data representative of the patient's condition, anatomy, pathology, medical history, preferences, and/or any other information or parameters relevant to the patient. For example, the patient data set 108 can include medical history, surgical intervention data, treatment outcome data, progress data (e.g., physician notes), patient feedback (e.g., feedback acquired using quality of life questionnaires, surveys), clinical data, provider information (e.g., physician, hospital, surgical team), patient information (e.g., demographics, sex, age, height, weight, type of pathology, occupation, activity level, tissue information, health rating, comorbidities, health related quality of life (HRQL)), vital signs, diagnostic results, medication information, allergies, image data (e.g., camera images, Magnetic Resonance Imaging (MRI) images, ultrasound images, Computerized Aided Tomography (CAT) scan images, Positron Emission Tomography (PET) images, X-Ray images), diagnostic equipment information (e.g., manufacturer, model number, specifications, user-selected settings/configurations, etc.), or the like. In some embodiments, the patient data set 108 includes data representing one or more of patient identification number (ID), age, gender, body mass index (BMI), lumbar lordosis, Cobb angle(s), pelvic incidence, disc height, segment flexibility, bone quality, rotational displacement, and/or treatment level of the spine.

The client computing device 102 is operably connected via a communication network 104 to a server 106, thus allowing for data transfer between the client computing device 102 and the server 106. The communication network 104 may be a wired and/or a wireless network. The communication network 104, if wireless, may be implemented using communication techniques such as Visible Light Communication (VLC), Worldwide Interoperability for Microwave Access (WiMAX), Long term evolution (LTE), Wireless local area network (WLAN), Infrared (IR) communication, Public Switched Telephone Network (PSTN), Radio waves, and/or other communication techniques known in the art.

The server 106, which may also be referred to as a "treatment assistance network" or "prescriptive analytics network," can include one or more computing devices and/or systems. As discussed further herein, the server 106 can include one or more processors, and memory storing instructions executable by the one or more processors to perform the methods described herein. In some embodiments, the server 106 is implemented as a distributed "cloud" computing system or facility across any suitable combination of hardware and/or virtual computing resources.

The client computing device 102 and server 106 can individually or collectively perform the various methods described herein for providing patient-specific medical care. For example, some or all of the steps of the methods described herein can be performed by the client computing device 102 alone, the server 106 alone, or a combination of the client computing device 102 and the server 106. Thus, although certain operations are described herein with respect to the server 106, it shall be appreciated that these operations can also be performed by the client computing device 102, and vice-versa.

The server 106 includes at least one database 110 configured to store reference data useful for the treatment planning methods described herein. The reference data can include historical and/or clinical data from the same or other patients, data collected from prior surgeries and/or other treatments of patients by the same or other healthcare providers, data relating to medical device designs, data collected from study groups or research groups, data from practice databases, data from academic institutions, data from implant manufacturers or other medical device manufacturers, data from imaging studies, data from simulations, clinical trials, demographic data, treatment data, outcome data, mortality rates, or the like.

In some embodiments, the database 110 includes a plurality of reference patient data sets, each patient reference data set associated with a corresponding reference patient. For example, the reference patient can be a patient that previously received treatment or is currently receiving treatment. Each reference patient data set can include data representative of the corresponding reference patient's condition, anatomy, pathology, medical history, disease progression, preferences, and/or any other information or parameters relevant to the reference patient, such as any of the data described herein with respect to the patient data set 108. In some embodiments, the reference patient data set includes pre-operative data, intra-operative data, and/or post-operative data. For example, a reference patient data set can include data representing one or more of patient ID, age, gender, BMI, lumbar lordosis, Cobb angle(s), pelvic incidence, disc height, segment flexibility, bone quality, rotational displacement, and/or treatment level of the spine. As another example, a reference patient data set can include treatment data regarding at least one treatment procedure performed on the reference patient, such as descriptions of surgical procedures or interventions (e.g., surgical approaches, bony resections, surgical maneuvers, corrective maneuvers, placement of implants or other devices). In some embodiments, the treatment data includes medical device design data for at least one medical device used to treat the reference patient, such as physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties). In yet another example, a reference patient data set can include outcome data representing an outcome of the treatment of the reference patient, such as corrected anatomical metrics, presence of fusion, HRQL, activity level, return to work, complications, recovery times, efficacy, mortality, and/or follow-up surgeries.

In some embodiments, the server 106 receives at least some of the reference patient data sets from a plurality of healthcare provider computing systems (e.g., systems 112a-112c, collectively 112). The server 106 can be connected to the healthcare provider computing systems 112 via one or more communication networks (not shown). Each healthcare provider computing system 112 can be associated with a corresponding healthcare provider (e.g., physician, surgeon, medical clinic, hospital, healthcare network, etc.). Each healthcare provider computing system 112 can include at least one reference patient data set (e.g., reference patient data sets 114a-114c, collectively 114) associated with reference patients treated by the corresponding healthcare provider. The reference patient data sets 114 can include, for example, electronic medical records, electronic health records, biomedical data sets, etc. The reference patient data sets 114 can be received by the server 106 from the healthcare provider computing systems 112 and can be reformatted into different formats for storage in the database 110. Optionally, the reference patient data sets 114 can be processed (e.g., cleaned) to ensure that the represented patient parameters are likely to be useful in the treatment planning methods described herein.

As described in further detail herein, the server 106 can be configured with one or more algorithms that generate patient-specific treatment plan data (e.g., treatment procedures, medical devices) based on the reference data. In some embodiments, the patient-specific data is generated based on correlations between the patient data set 108 and the reference data. Optionally, the server 106 can predict outcomes, including recovery times, efficacy based on clinical end points, likelihood of success, predicted mortality, predicted related follow-up surgeries, or the like. In some embodiments, the server 106 can continuously or periodically analyze patient data (including patient data obtained during the patient stay) to determine near real-time or real-time risk scores, mortality prediction, etc.

In some embodiments, the server 106 includes one or more modules for performing one or more steps of the patient-specific treatment planning methods described herein. For example, in the depicted embodiment, the server 106 includes a data analysis module 116 and a treatment planning module 118. In alternative embodiments, one or more of these modules may be combined with each other, or may be omitted. Thus, although certain operations are described herein with respect to a particular module or modules, this is not intended to be limiting, and such operations can be performed by a different module or modules in alternative embodiments.

The data analysis module 116 is configured with one or more algorithms for identifying a subset of reference data from the database 110 that is likely to be useful in developing a patient-specific treatment plan. For example, the data analysis module 116 can compare patient-specific data (e.g., the patient data set 108 received from the client computing device 102) to the reference data from the database 110 (e.g., the reference patient data sets) to identify similar data (e.g., one or more similar patient data sets in the reference patient data sets). The comparison can be based on one or more parameters, such as age, gender, BMI, lumbar lordosis, pelvic incidence, and/or treatment levels. The parameter(s) can be used to calculate a similarity score for each reference patient. The similarity score can represent a statistical correlation between the patient data set 108 and the reference patient data set. Accordingly, similar patients can be identified based on whether the similarity score is above, below, or at a specified threshold value. For example, as described in greater detail below, the comparison can be performed by assigning values to each parameter and determining the aggregate difference between the subject patient and each reference patient. Reference patients whose aggregate difference is below a threshold can be considered to be similar patients.

The data analysis module 116 can further be configured with one or more algorithms to select a subset of the reference patient data sets, e.g., based on similarity to the patient data set 108 and/or treatment outcome of the corresponding reference patient. For example, the data analysis module 116 can identify one or more similar patient data sets in the reference patient data sets, and then select a subset of the similar patient data sets based on whether the similar patient data set includes data indicative of a favorable or desired treatment outcome. The outcome data can include data representing one or more outcome parameters, such as corrected anatomical metrics, presence of fusion, HRQL, activity level, complications, recovery times, efficacy, mortality, or follow-up surgeries. As described in further detail below, in some embodiments, the data analysis module 116 calculates an outcome score by assigning values to each outcome parameter. A patient can be considered to have a favorable outcome if the outcome score is above, below, or at a specified threshold value.

In some embodiments, the data analysis module 116 selects a subset of the reference patient data sets based at least in part on user input (e.g., from a clinician, surgeon, physician, healthcare provider). For example, the user input can be used in identifying similar patient data sets. In some embodiments, weighting of similarity and/or outcome parameters can be selected by a healthcare provider or physician to adjust the similarity and/or outcome score based on clinician input. In further embodiments, the healthcare provider or physician can select the set of similarity and/or outcome parameters (or define new similarity and/or outcome parameters) used to generate the similarity and/or outcome score, respectively.

In some embodiments, the data analysis module 116 includes one or more algorithms used to select a set or subset of the reference patient data sets based on criteria other than patient parameters. For example, the one or more algorithms can be used to select the subset based on healthcare provider parameters (e.g., based on healthcare provider ranking/scores such as hospital/physician expertise, number of procedures performed, hospital ranking, etc.) and/or healthcare resource parameters (e.g., diagnostic equipment, facilities, surgical equipment such as surgical robots), or other non-patient related information that can be used to predict outcomes and risk profiles for procedures for the present healthcare provider. For example, reference patient data sets with images captured from similar diagnostic equipment can be aggregated to reduce or limit irregularities due to variation between diagnostic equipment. Additionally, patient-specific treatment plans can be developed for a particular health-care provider using data from similar healthcare providers (e.g., healthcare providers with traditionally similar outcomes, physician expertise, surgical teams, etc.). In some embodiments, reference healthcare provider data sets, hospital data sets, physician data sets, surgical team data sets, post-treatment data set, and other data sets can be utilized. By way of example, a patient-specific treatment plan to perform a battlefield surgery can be based on reference patient data from similar battlefield surgeries and/or datasets associated with battlefield surgeries. In another example, the patient-specific treatment plan can be generated based on available robotic surgical systems. The reference patient data sets can be selected based on patients that have been operated on using comparable robotic surgical systems under similar conditions (e.g., size and capabilities of surgical teams, hospital resources, etc.).

The treatment planning module 118 is configured with one or more algorithms to generate at least one treatment plan (e.g., pre-operative plans, surgical plans, post-operative plans etc.) based on the output from the data analysis module 116. In some embodiments, the treatment planning module 118 is configured to develop and/or implement at least one predictive model for generating the patient-specific treatment plan, also known as a "prescriptive model." The predictive model(s) can be developed using clinical knowledge, statistics, machine learning, AI, neural networks, or the like. In some embodiments, the output from the data analysis module 116 is analyzed (e.g., using statistics, machine learning, neural networks, AI) to identify correlations between data sets, patient parameters, healthcare provider parameters, healthcare resource parameters, treatment procedures, medical device designs, and/or treatment outcomes. These correlations can be used to develop at least one predictive model that predicts the likelihood that a treatment plan will produce a favorable outcome for the particular patient. The predictive model(s) can be validated, e.g., by inputting data into the model(s) and comparing the output of the model to the expected output.

In some embodiments, the treatment planning module 118 is configured to generate the treatment plan based on previous treatment data from reference patients. For example, the treatment planning module 118 can receive a selected subset of reference patient data sets and/or similar patient data sets from the data analysis module 116, and determine or identify treatment data from the selected subset. The treatment data can include, for example, treatment procedure data (e.g., surgical procedure or intervention data) and/or medical device design data (e.g. implant design data) that are associated with favorable or desired treatment outcomes for the corresponding patient. The treatment planning module 118 can analyze the treatment procedure data and/or medical device design data to determine an optimal treatment protocol for the patient to be treated. For example, the treatment procedures and/or medical device designs can be assigned values and aggregated to produce a treatment score. The patient-specific treatment plan can be determined by selecting treatment plan(s) based on the score (e.g., higher or highest score; lower or lowest score; score that is above, below, or at a specified threshold value). The personalized patient-specific treatment plan can be based on, at least in part, the patient-specific technologies or patient-specific selected technology.

Alternatively or in combination, the treatment planning module 118 can generate the treatment plan based on correlations between data sets. For example, the treatment planning module 118 can correlate treatment procedure data and/or medical device design data from similar patients with favorable outcomes (e.g., as identified by the data analysis module 116). Correlation analysis can include transforming correlation coefficient values to values or scores. The values/scores can be aggregated, filtered, or otherwise analyzed to determine one or more statistical significances. These correlations can be used to determine treatment procedure(s) and/or medical device design(s) that are optimal or likely to produce a favorable outcome for the patient to be treated.

Alternatively or in combination, the treatment planning module 118 can generate the treatment plan using one or more AI techniques. AI techniques can be used to develop computing systems capable of simulating aspects of human intelligence, e.g., learning, reasoning, planning, problem solving, decision making, etc. AI techniques can include, but are not limited to, case-based reasoning, rule-based systems, artificial neural networks, decision trees, support vector machines, regression analysis, Bayesian networks (e.g., naïve Bayes classifiers), genetic algorithms, cellular automata, fuzzy logic systems, multi-agent systems, swarm intelligence, data mining, machine learning (e.g., supervised learning, unsupervised learning, reinforcement learning), and hybrid systems.

In some embodiments, the treatment planning module 118 generates the treatment plan using one or more trained machine learning models. Various types of machine learning models, algorithms, and techniques are suitable for use with the present technology. In some embodiments, the machine learning model is initially trained on a training data set, which is a set of examples used to fit the parameters (e.g., weights of connections between "neurons" in artificial neural networks) of the model. For example, the training data set can include any of the reference data stored in database 110, such as a plurality of reference patient data sets or a selected subset thereof (e.g., a plurality of similar patient data sets).

In some embodiments, the machine learning model (e.g., a neural network or a naïve Bayes classifier) may be trained on the training data set using a supervised learning method (e.g., gradient descent or stochastic gradient descent). The training dataset can include pairs of generated "input vectors" with the associated corresponding "answer vector" (commonly denoted as the target). The current model is run with the training data set and produces a result, which is then compared with the target, for each input vector in the training data set. Based on the result of the comparison and the specific learning algorithm being used, the parameters of the model are adjusted. The model fitting can include both variable selection and parameter estimation. The fitted model can be used to predict the responses for the observations in a second data set called the validation data set. The validation data set can provide an unbiased evaluation of a model fit on the training data set while tuning the model parameters. Validation data sets can be used for regularization by early stopping, e.g., by stopping training when the error on the validation data set increases, as this may be a sign of overfitting to the training data set. In some embodiments, the error of the validation data set error can fluctuate during training, such that ad-hoc rules may be used to decide when overfitting has truly begun. Finally, a test data set can be used to provide an unbiased evaluation of a final model fit on the training data set.

To generate a treatment plan, the patient data set 108 can be input into the trained machine learning model(s). Additional data, such as the selected subset of reference patient data sets and/or similar patient data sets, and/or treatment data from the selected subset, can also be input into the trained machine learning model(s). The trained machine learning model(s) can then calculate whether various candidate treatment procedures and/or medical device designs are likely to produce a favorable outcome for the patient. Based on these calculations, the trained machine learning model(s) can select at least one treatment plan for the patient. In embodiments where multiple trained machine learning models are used, the models can be run sequentially or concurrently to compare outcomes and can be periodically updated using training data sets. The treatment planning module 118 can use one or more of the machine learning models based the model's predicted accuracy score.

The patient-specific treatment plan generated by the treatment planning module 118 can include at least one patient-specific treatment procedure (e.g., a surgical procedure or intervention) and/or at least one patient-specific medical device (e.g., an implant or implant delivery instrument). A patient-specific treatment plan can include an entire surgical procedure or portions thereof. Additionally, one or more patient-specific medical devices can be specifically selected or designed for the corresponding surgical procedure, thus allowing for the various components of the patient-specific technology to be used in combination to treat the patient.

In some embodiments, the patient-specific treatment procedure includes an orthopedic surgery procedure, such as spinal surgery, hip surgery, knee surgery, jaw surgery, hand surgery, shoulder surgery, elbow surgery, total joint reconstruction (arthroplasty), skull reconstruction, foot surgery, or ankle surgery. Spinal surgery can include spinal fusion surgery, such as posterior lumbar interbody fusion (PLIF), anterior lumbar interbody fusion (ALIF), transverse or transforaminal lumbar interbody fusion (TLIF), lateral lumbar interbody fusion (LLIF), direct lateral lumbar interbody fusion (DLIF), or extreme lateral lumbar interbody fusion (XLIF). In some embodiments, the patient-specific treatment procedure includes descriptions of and/or instructions for performing one or more aspects of a patient-specific surgical procedure. For example, the patient-specific surgical procedure can include one or more of a surgical approach, a corrective maneuver, a bony resection, or implant placement.

In some embodiments, the patient-specific medical device design includes a design for an orthopedic implant and/or a design for an instrument for delivering an orthopedic implant. Examples of such implants include, but are not limited to, screws (e.g., bone screws, spinal screws, pedicle screws, facet screws), interbody implant devices (e.g., intervertebral implants), cages, plates, rods, disks, fusion devices, spacers, rods, expandable devices, stents, brackets, ties, scaffolds, fixation device, anchors, nuts, bolts, rivets, connectors, tethers, fasteners, joint replacements, hip implants, or the like. Examples of instruments include, but are not limited to, screw guides, cannulas, ports, catheters, insertion tools, or the like.

A patient-specific medical device design can include data representing one or more of physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties) of a corresponding medical device. For example, a design for an orthopedic implant can include implant shape, size, material, and/or effective stiffness (e.g., lattice density, number of struts, location of struts, etc.). In some embodiments, the generated patient-specific medical device design is a design for an entire device. Alternatively, the generated design can be for one or more components of a device, rather than the entire device.

In some embodiments, the design is for one or more patient-specific device components that can be used with standard, off-the-shelf components. For example, in a spinal surgery, a pedicle screw kit can include both standard components and patient-specific customized components. In some embodiments, the generated design is for a patient-specific medical device that can be used with a standard, off-the-shelf delivery instrument. For example, the implants (e.g., screws, screw holders, rods) can be designed and manufactured for the patient, while the instruments for delivering the implants can be standard instruments. This approach allows the components that are implanted to be designed and manufactured based on the patient's anatomy and/or surgeon's preferences to enhance treatment. The patient-specific devices described herein are expected to improve delivery into the patient's body, placement at the treatment site, and/or interaction with the patient's anatomy.

In embodiments where the patient-specific treatment plan includes a surgical procedure to implant a medical device, the treatment planning module 118 can also store various types of implant surgery information, such as implant parameters (e.g., types, dimensions), availability of implants, aspects of a pre-operative plan (e.g., initial implant configuration, detection and measurement of the patient's anatomy, etc.), FDA requirements for implants (e.g., specific implant parameters and/or characteristics for compliance with FDA regulations), or the like. In some embodiments, the treatment planning module 118 can convert the implant surgery information into formats useable for machine-learning based models and algorithms. For example, the implant surgery information can be tagged with particular identifiers for formulas or can be converted into numerical representations suitable for supplying to the trained machine learning model(s). The treatment planning module 118 can also store information regarding the patient's anatomy, such as two- or three-dimensional images or models of the anatomy, and/or information regarding the biology, geometry, and/or mechanical properties of the anatomy. The anatomy information can be used to inform implant design and/or placement.

The treatment plan(s) generated by the treatment planning module 118 can be transmitted via the communication network 104 to the client computing device 102 for output to a user (e.g., clinician, surgeon, healthcare provider, patient). In some embodiments, the client computing device 102 includes or is operably coupled to a display 122 for outputting the treatment plan(s). The display 122 can include a graphical user interface (GUI) for visually depicting various aspects of the treatment plan(s). For example, the display 122 can show various aspects of a surgical procedure to be performed on the patient, such as the surgical approach, treatment levels, corrective maneuvers, tissue resection, and/or implant placement. To facilitate visualization, a virtual model of the surgical procedure can be displayed. As another example, the display 122 can show a design for a medical device to be implanted in the patient, such as a two- or three-dimensional model of the device design. The display 122 can also show patient information, such as two- or three-dimensional images or models of the patient's anatomy where the surgical procedure is to be performed and/or where the device is to be implanted. The client computing device 102 can further include one or more user input devices (not shown) allowing the user to modify, select, approve, and/or reject the displayed treatment plan(s).

In some embodiments, the medical device design(s) generated by the treatment planning module 118 can be transmitted from the client computing device 102 and/or server 106 to a manufacturing system 124 for manufacturing a corresponding medical device. The manufacturing system 124 can be located on site or off site. On-site manufacturing can reduce the number of sessions with a patient and/or the time to be able to perform the surgery whereas off-site manufacturing can be useful make the complex devices. Off-site manufacturing facilities can have specialized manufacturing equipment. In some embodiments, more complicated device components can be manufactured off site, while simpler device components can be manufactured on site.

Various types of manufacturing systems are suitable for use in accordance with the embodiments herein. For example, the manufacturing system 124 can be configured for additive manufacturing, such as three-dimensional (3D) printing, stereolithography (SLA), digital light processing (DLP), fused deposition modeling (FDM), selective laser sintering (SLS), selective laser melting (SLM), selective heat sintering (SHM), electronic beam melting (EBM), laminated object manufacturing (LOM), powder bed printing (PP), thermoplastic printing, direct material deposition (DMD), inkjet photo resin printing, or like technologies, or combination thereof. Alternatively or in combination, the manufacturing system 124 can be configured for subtractive (traditional) manufacturing, such as CNC machining, electrical discharge machining (EDM), grinding, laser cutting, water jet machining, manual machining (e.g., milling, lathe/turning), or like technologies, or combinations thereof. The manufacturing system 124 can manufacture one or more patient-specific medical devices based on fabrication instructions or data (e.g., CAD data, 3D data, digital blueprints, stereolithography data, or other data suitable for the various manufacturing technologies described herein). Different components of the system 100 can generate at least a portion of the manufacturing data used by the manufacturing system 124. The manufacturing data can include, without limitation, fabrication instructions (e.g., programs executable by additive manufacturing equipment, subtractive manufacturing equipment, etc.), 3D data, CAD data (e.g., CAD files), CAM data (e.g., CAM files), path data (e.g., print head paths, tool paths, etc.), material data, tolerance data, surface finish data (e.g., surface roughness data), regulatory data (e.g., FDA requirements, reimbursement data, etc.), or the like. The manufacturing system 124 can analyze the manufacturability of the implant design based on the received manufacturing data. The implant design can be finalized by altering geometries, surfaces, etc. and then generating manufacturing instructions. In some embodiments, the server 106 generates at least a portion of the manufacturing data, which is transmitted to the manufacturing system 124.

The manufacturing system 124 can generate CAM data, print data (e.g., powder bed print data, thermoplastic print data, photo resin data, etc.), or the like and can include additive manufacturing equipment, subtractive manufacturing equipment, thermal processing equipment, or the like. The additive manufacturing equipment can be 3D printers, stereolithography devices, digital light processing devices, fused deposition modeling devices, selective laser sintering devices, selective laser melting devices, electronic beam melting devices, laminated object manufacturing devices, powder bed printers, thermoplastic printers, direct material deposition devices, or inkjet photo resin printers, or like technologies. The subtractive manufacturing equipment can be CNC machines, electrical discharge machines, grinders, laser cutters, water jet machines, manual machines (e.g., milling machines, lathes, etc.), or like technologies. Both additive and subtractive techniques can be used to produce implants with complex geometries, surface finishes, material properties, etc. The generated fabrication instructions can be configured to cause the manufacturing system 124 to manufacture the patient-specific orthopedic implant that matches or is therapeutically the same as the patient-specific design. In some embodiments, the patient-specific medical device can include features, materials, and designs shared across designs to simplify manufacturing. For example, deployable patient-specific medical devices for different patients can have similar internal deployment mechanisms but have different deployed configurations. In some embodiments, the components of the patient-specific medical devices are selected from a set of available pre-fabricated components and the selected pre-fabricated components can be modified based on the fabrication instructions or data.

The treatment plans described herein can be performed by a surgeon, a surgical robot, or a combination thereof, thus allowing for treatment flexibility. In some embodiments, the surgical procedure can be performed entirely by a surgeon, entirely by a surgical robot, or a combination thereof. For example, one step of a surgical procedure can be manually performed by a surgeon and another step of the procedure can be performed by a surgical robot. In some embodiments the treatment planning module 118 generates control instructions configured to cause a surgical robot (e.g., robotic surgery systems, navigation systems, etc.) to partially or fully perform a surgical procedure. The control instructions can be transmitted to the robotic apparatus by the client computing device 102 and/or the server 106.

Following the treatment of the patient in accordance with the treatment plan, treatment progress can be monitored over one or more time periods to update the data analysis module 116 and/or treatment planning module 118. Post-treatment data can be added to the reference data stored in the database 110. The post-treatment data can be used to train machine learning models for developing patient-specific treatment plans, patient-specific medical devices, or combinations thereof.

It shall be appreciated that the components of the system 100 can be configured in many different ways. For example, in alternative embodiments, the database 110, the data analysis module 116 and/or the treatment planning module 118 can be components of the client computing device 102, rather than the server 106. As another example, the database 110 the data analysis module 116, and/or the treatment planning module 118 can be located across a plurality of different servers, computing systems, or other types of cloud-computing resources, rather than at a single server 106 or client computing device 102.

Additionally, in some embodiments, the system 100 can be operational with numerous other computing system environments or configurations. Examples of computing systems, environments, and/or configurations that may be suitable for use with the technology include, but are not limited to, personal computers, server computers, handheld or laptop devices, cellular telephones, wearable electronics, tablet devices, multiprocessor systems, microprocessor-based systems, programmable consumer electronics, network PCs, minicomputers, mainframe computers, distributed computing environments that include any of the above systems or devices, or the like.

Figure 2:
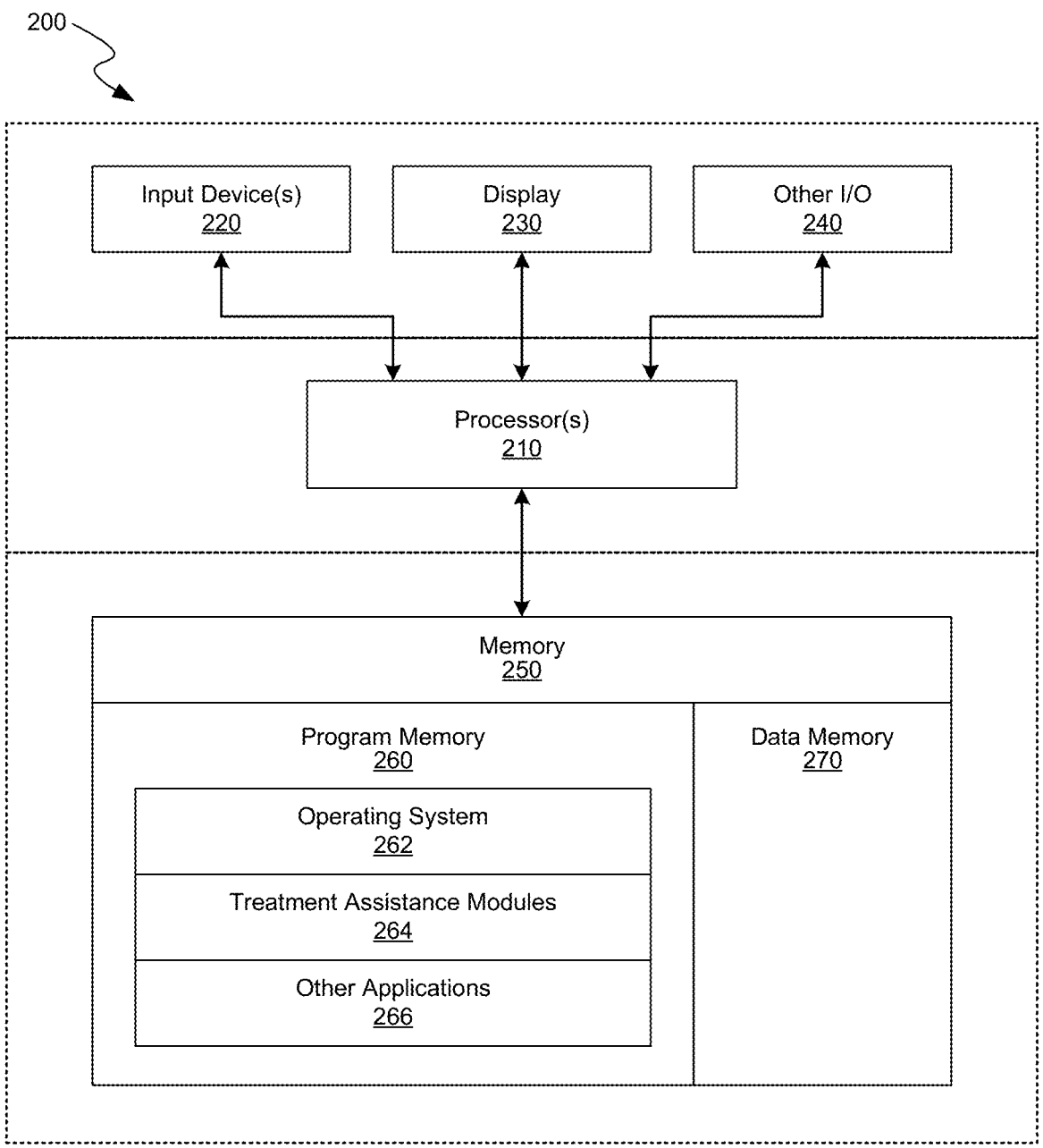
FIG. 2 illustrates a computing device suitable for use in connection with the system of FIG. 1, according to an embodiment.

FIG. 2 illustrates a computing device 200 suitable for use in connection with the system 100 of FIG. 1, according to an embodiment. The computing device 200 can be incorporated in various components of the system 100 of FIG. 1, such as the client computing device 102 or the server 106. The computing device 200 includes one or more processors 210 (e.g., CPU(s), GPU(s), HPU(s), etc.). The processor(s) 210 can be a single processing unit or multiple processing units in a device or distributed across multiple devices. The processor(s) 210 can be coupled to other hardware devices, for example, with the use of a bus, such as a PCI bus or SCSI bus. The processor(s) 210 can be configured to execute one more computer-readable program instructions, such as program instructions to carry out of any of the methods described herein.

The computing device 200 can include one or more input devices 220 that provide input to the processor(s) 210, e.g., to notify it of actions from a user of the device 200. The actions can be mediated by a hardware controller that interprets the signals received from the input device and communicates the information to the processor(s) 210 using a communication protocol. Input device(s) 220 can include, for example, a mouse, a keyboard, a touchscreen, an infrared sensor, a touchpad, a wearable input device, a camera- or image-based input device, a microphone, or other user input devices.

The computing device 200 can include a display 230 used to display various types of output, such as text, models, virtual procedures, surgical plans, implants, graphics, and/or images (e.g., images with voxels indicating radiodensity units or Hounsfield units representing the density of the tissue at a location). In some embodiments, the display 230 provides graphical and textual visual feedback to a user. The processor(s) 210 can communicate with the display 230 via a hardware controller for devices. In some embodiments, the display 230 includes the input device(s) 220 as part of the display 230, such as when the input device(s) 220 include a touchscreen or is equipped with an eye direction monitoring system. In alternative embodiments, the display 230 is separate from the input device(s) 220. Examples of display devices include an LCD display screen, an LED display screen, a projected, holographic, or augmented reality display (e.g., a heads-up display device or a head-mounted device), and so on.

Optionally, other I/O devices 240 can also be coupled to the processor(s) 210, such as a network card, video card, audio card, USB, firewire or other external device, camera, printer, speakers, CD-ROM drive, DVD drive, disk drive, or Blu-Ray device. Other I/O devices 240 can also include input ports for information from directly connected medical equipment such as imaging apparatuses, including MRI machines, X-Ray machines, CT machines, etc. Other I/O devices 240 can further include input ports for receiving data from these types of machine from other sources, such as across a network or from previously captured data, for example, stored in a database.

In some embodiments, the computing device 200 also includes a communication device (not shown) capable of communicating wirelessly or wire-based with a network node. The communication device can communicate with another device or a server through a network using, for example, TCP/IP protocols. The computing device 200 can utilize the communication device to distribute operations across multiple network devices, including imaging equipment, manufacturing equipment, etc.

The computing device 200 can include memory 250, which can be in a single device or distributed across multiple devices. Memory 250 includes one or more of various hardware devices for volatile and non-volatile storage, and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. In some embodiments, the memory 250 is a non-transitory computer-readable storage medium that stores, for example, programs, software, data, or the like. In some embodiments, memory 250 can include program memory 260 that stores programs and software, such as an operating system 262, one or more treatment assistance modules 264, and other application programs 266. The treatment assistance module(s) 264 can include one or more modules configured to perform the various methods described herein (e.g., the data analysis module 116 and/or treatment planning module 118 described with respect to FIG. 1). Memory 250 can also include data memory 270 that can include, e.g., reference data, configuration data, settings, user options or preferences, etc., which can be provided to the program memory 260 or any other element of the computing device 200.

Figure 3:
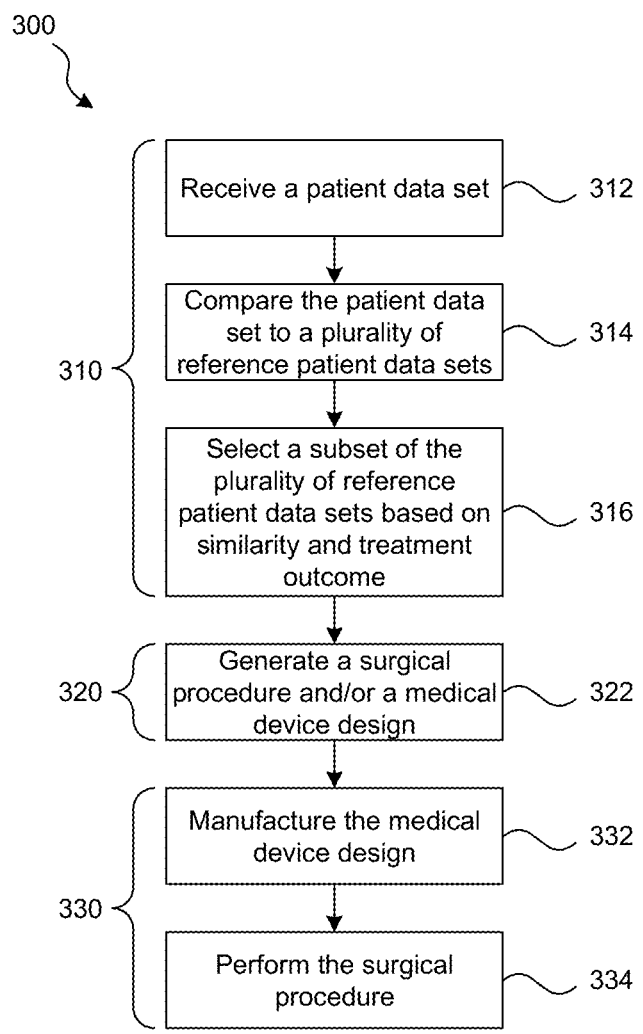
FIG. 3 is a flow diagram illustrating a method for providing patient-specific medical care, according to an embodiment.

FIG. 3 is a flow diagram illustrating a method 300 for providing patient-specific medical care, according to an embodiment. The method 300 can include a data phase 310, a modeling phase 320, and an execution phase 330. The data phase 310 can include collecting data of a patient to be treated (e.g., pathology data), and comparing the patient data to reference data (e.g., prior patient data such as pathology, surgical, and/or outcome data). For example, a patient data set can be received (block 312). The patient data set can be compared to a plurality of reference patient data sets (block 314), e.g., in order to identify one or more similar patient data sets in the plurality of reference patient data sets. Each of the plurality of reference patient data sets can include data representing one or more of age, gender, BMI, lumbar lordosis, Cobb angle(s), pelvic incidence, disc height, segment flexibility, bone quality, rotational displacement, or treatment level of the spine.

A subset of the plurality of reference patient data sets can be selected (block 316), e.g., based on similarity to the patient data set and/or treatment outcomes of the corresponding reference patients. For example, a similarity score can be generated for each reference patient data set, based on the comparison of the patient data set and the reference patient data set. The similarity score can represent a statistical correlation between the patient data and the reference patient data set. One or more similar patient data sets can be identified based, at least partly, on the similarity score.

In some embodiments, each patient data set of the selected subset includes and/or is associated with data indicative of a favorable treatment outcome (e.g., a favorable treatment outcome based on a single target outcome, aggregate outcome score, outcome thresholding). The data can include, for example, data representing one or more of corrected anatomical metrics, presence of fusion, health related quality of life, activity level, or complications. In some embodiments, the data is or includes an outcome score, which can be calculated based on a single target outcome, an aggregate outcome, and/or an outcome threshold.

Optionally, the data analysis phase 310 can include identifying or determining, for at least one patient data set of the selected subset (e.g., for at least one similar patient data set), surgical procedure data and/or medical device design data associated with the favorable treatment outcome. The surgical procedure data can include data representing one or more of a surgical approach, a corrective maneuver, a bony resection, or implant placement. The at least one medical device design can include data representing one or more of physical properties, mechanical properties, or biological properties of a corresponding medical device. In some embodiments, the at least one patient-specific medical device design includes a design for an implant or an implant delivery instrument.

In the modeling phase 320, a surgical procedure and/or medical device design is generated (block 322). The generating step can include developing at least one predictive model based on the patient data set and/or selected subset of reference patient data sets (e.g., using statistics, machine learning, neural networks, AI, or the like). The predictive model can be configured to generate the surgical procedure and/or medical device design.

In some embodiments, the predictive model includes one or more trained machine learning models that generate, at least partly, the surgical procedure and/or medical device design. For example, the trained machine learning model(s) can determine a plurality of candidate surgical procedures and/or medical device designs for treating the patient. Each surgical procedure can be associated with a corresponding medical device design. In some embodiments, the surgical procedures and/or medical device designs are determined based on surgical procedure data and/or medical device design data associated with favorable outcomes, as previously described with respect to the data analysis phase 310. For each surgical procedure and/or corresponding medical device design, the trained machine learning model(s) can calculate a probability of achieving a target outcome (e.g., favorable or desired outcome) for the patient. The trained machine learning model(s) can then select at least one surgical procedure and/or corresponding medical device design based, at least partly, on the calculated probabilities.

The execution phase 330 can include manufacturing the medical device design (block 332). In some embodiments, the medical device design is manufactured by a manufacturing system configured to perform one or more of additive manufacturing, 3D printing, stereolithography, digital light processing, fused deposition modeling, selective laser sintering, selective laser melting, electronic beam melting, laminated object manufacturing, powder bed printing, thermoplastic printing, direct material deposition, or inkjet photo resin printing. The execution phase 330 can optionally include generating fabrication instructions configured to cause the manufacturing system to manufacture a medical device having the medical device design.

The execution phase 330 can include performing the surgical procedure (block 334). The surgical procedure can involve implanting a medical device having the medical device design into the patient. The surgical procedure can be performed manually, by a surgical robot, or a combination thereof. In embodiments where the surgical procedure is performed by a surgical robot, the execution phase 330 can include generating control instructions configured to cause the surgical robot to perform, at least partly, the patient-specific surgical procedure.

The method 300 can be implemented and performed in various ways. In some embodiments, one or more steps of the method 300 (e.g., the data phase 310 and/or the modeling phase 320) can be implemented as computer-readable instructions stored in memory and executable by one or more processors of any of the computing devices and systems described herein (e.g., the system 100), or a component thereof (e.g., the client computing device 102 and/or the server 106). Alternatively, one or more steps of the method 300 (e.g., the execution phase 330) can be performed by a healthcare provider (e.g., physician, surgeon), a robotic apparatus (e.g., a surgical robot), a manufacturing system (e.g., manufacturing system 124), or a combination thereof. In some embodiments, one or more steps of the method 300 are omitted (e.g., the execution phase 330).

FIGS. 4A-4C illustrate exemplary data sets that may be used and/or generated in connection with the methods described herein (e.g., the data analysis phase 310 described with respect to FIG. 3), according to an embodiment. FIG. 4A illustrates a patient data set 400 of a patient to be treated. The patient data set 400 can include a patient ID and a plurality of pre-operative patient metrics (e.g., age, gender, BMI, lumbar lordosis (LL), pelvic incidence (PI), and treatment levels of the spine (levels)). FIG. 4B illustrates a plurality of reference patient data sets 410. In the depicted embodiment, the reference patient data sets 410 include a first subset 412 from a study group (Study Group X), a second subset 414 from a practice database (Practice Y), and a third subset 416 from an academic group (University Z). In alternative embodiments, the reference patient data sets 410 can include data from other sources, as previously described herein. Each reference patient data set can include a patient ID, a plurality of pre-operative patient metrics (e.g., age, gender, BMI, lumbar lordosis (LL), pelvic incidence (PI), and treatment levels of the spine (levels)), treatment outcome data (Outcome) (e.g., presence of fusion (fused), HRQL, complications), and treatment procedure data (Surg. Intervention) (e.g., implant design, implant placement, surgical approach).

FIG. 4C illustrates comparison of the patient data set 400 to the reference patient data sets 410. As previously described, the patient data set 400 can be compared to the reference patient data sets 410 to identify one or more similar patient data sets from the reference patient data sets.

In some embodiments, the patient metrics from the reference patient data sets 410 are converted to numeric values and compared the patient metrics from the patient data set 400 to calculate a similarity score 420 ("Pre-op Similarity") for each reference patient data set. Reference patient data sets having a similarity score below a threshold value can be considered to be similar to the patient data set 400. For example, in the depicted embodiment, reference patient data set 410a has a similarity score of 9, reference patient data set 410b has a similarity score of 2, reference patient data set 410c has a similarity score of 5, and reference patient data set 410d has a similarity score of 8. Because each of these scores are below the threshold value of 10, reference patient data sets 410a-d are identified as being similar patient data sets.

The treatment outcome data of the similar patient data sets 410a-d can be analyzed to determine surgical procedures and/or implant designs with the highest probabilities of success. For example, the treatment outcome data for each reference patient data set can be converted to a numerical outcome score 430 ("Outcome Quotient") representing the likelihood of a favorable outcome. In the depicted embodiment, reference patient data set 410a has an outcome score of 1, reference patient data set 410b has an outcome score of 1, reference patient data set 410c has an outcome score of 9, and reference patient data set 410d has an outcome score of 2. In embodiments where a lower outcome score correlates to a higher likelihood of a favorable outcome, reference patient data sets 410a, 410b, and 410d can be selected. The treatment procedure data from the selected reference patient data sets 410a, 410b, and 410d can then be used to determine at least one surgical procedure (e.g., implant placement, surgical approach) and/or implant design that is likely to produce a favorable outcome for the patient to be treated.

In some embodiments, a method for providing medical care to a patient is provided. The method can include comparing a patient data set to reference data. The patient data set and reference data can include any of the data types described herein. The method can include identifying and/or selecting relevant reference data (e.g., data relevant to treatment of the patient, such as data of similar patients and/or data of similar treatment procedures), using any of the techniques described herein. A treatment plan can be generated based on the selected data, using any of the techniques described herein. The treatment plan can include one or more treatment procedures (e.g., surgical procedures, instructions for procedures, models or other virtual representations of procedures), one or more medical devices (e.g., implanted devices, instruments for delivering devices, surgical kits), or a combination thereof.

In some embodiments, a system for generating a medical treatment plan is provided. The system can compare a patient data set to a plurality of reference patient data sets, using any of the techniques described herein. A subset of the plurality of reference patient data sets can be selected, e.g., based on similarity and/or treatment outcome, or any other technique as described herein. A medical treatment plan can be generated based at least in part on the selected subset, using any of the techniques described herein. The medical treatment plan can include one or more treatment procedures, one or more medical devices, or any of the other aspects of a treatment plan described herein, or combinations thereof.

In further embodiments, a system is configured to use historical patient data. The system can select historical patient data to develop or select a treatment plan, design medical devices, or the like. Historical data can be selected based on one or more similarities between the present patient and prior patients to develop a prescriptive treatment plan designed for desired outcomes. The prescriptive treatment plan can be tailored for the present patient to increase the likelihood of the desired outcome. In some embodiments, the system can analyze and/or select a subset of historical data to generate one or more treatment procedures, one or more medical devices, or a combination thereof. In some embodiments, the system can use subsets of data from one or more groups of prior patients, with favorable outcomes, to produce a reference historical data set used to, for example, design, develop or select the treatment plan, medical devices, or combinations thereof.

Figure 5:
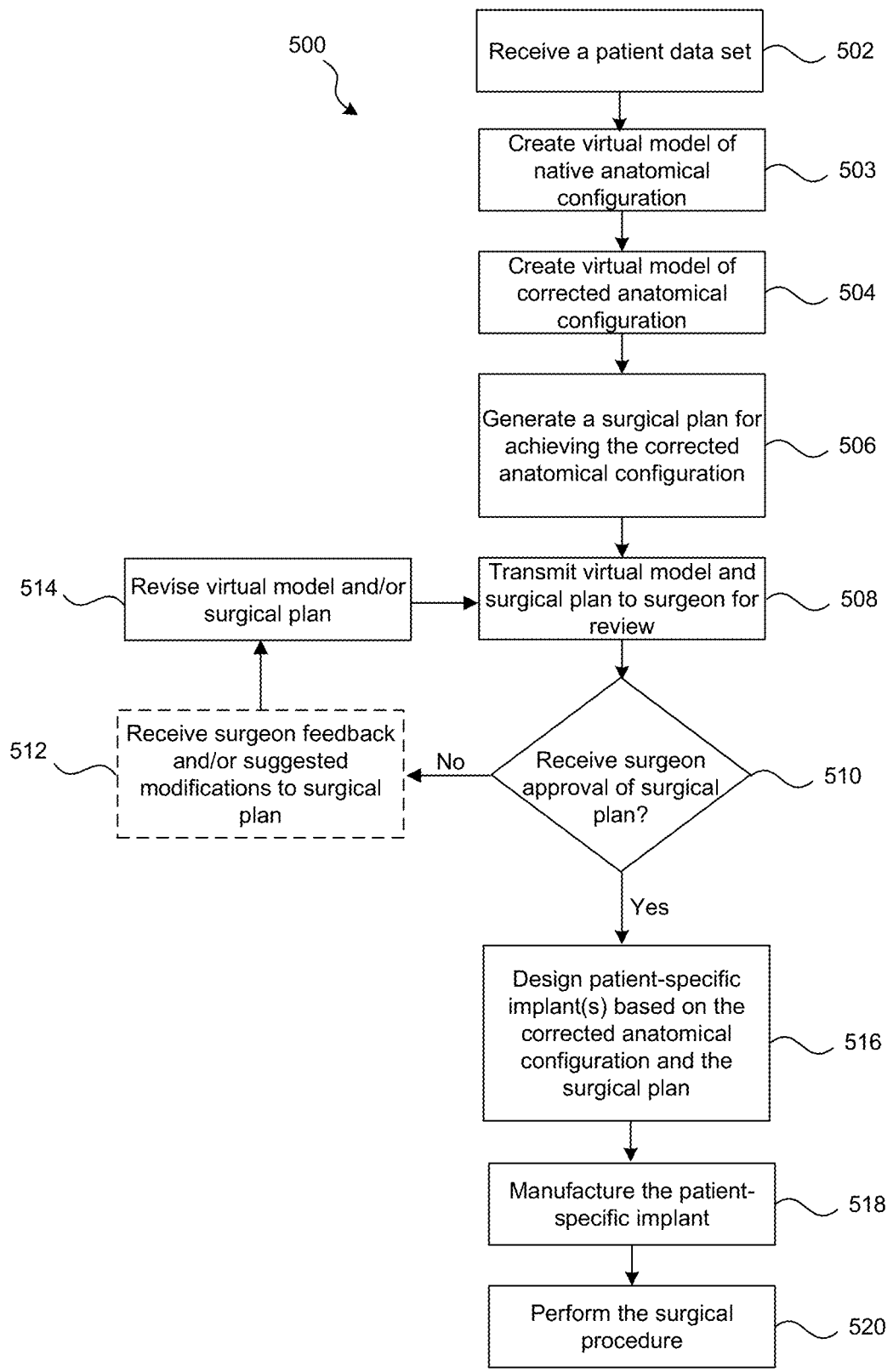
FIG. 5 is a flow diagram illustrating another method for providing patient-specific medical care, according to an embodiment.

FIG. 5 is a flow diagram illustrating a method 500 for providing patient-specific medical care, according to another embodiment of the present technology. The method 500 can begin in step 502 by receiving a patient data set for a particular patient in need of medical treatment. The patient data set can include data representative of the patient's condition, anatomy, pathology, symptoms, medical history, preferences, and/or any other information or parameters relevant to the patient. For example, the patient data set 808 can include surgical intervention data, treatment outcome data, progress data (e.g., surgeon notes), patient feedback (e.g., feedback acquired using quality of life questionnaires, surveys), clinical data, patient information (e.g., demographics, sex, age, height, weight, type of pathology, occupation, activity level, tissue information, health rating, comorbidities, health related quality of life (HRQL)), vital signs, diagnostic results, medication information, allergies, diagnostic equipment information (e.g., manufacturer, model number, specifications, user-selected settings/configurations, etc.) or the like. The patient data set can also include image data, such as camera images, Magnetic Resonance Imaging (MRI) images, ultrasound images, Computerized Aided Tomography (CAT) scan images, Positron Emission Tomography (PET) images, X-Ray images, and the like. In some embodiments, the patient data set includes data representing one or more of patient identification number (ID), age, gender, body mass index (BMI), lumbar lordosis, Cobb angle(s), pelvic incidence, disc height, segment flexibility, bone quality, rotational displacement, and/or treatment level of the spine. The patient data set can be received at a server, computing device, or other computing system. For example, in some embodiments the patient data set can be received by the server 106 shown in FIG. 1 or the computing system 606 described below with respect to FIG. 6. In some embodiments, the computing system that receives the patient data set in step 502 also stores one or more software modules (e.g., the data analysis module 116 and/or the treatment planning module 118, shown in FIG. 1, or additional software modules for performing various operations of the method 500). Additional details for collecting and receiving the patient data set are described below with respect to FIGS. 6-7D.

In some embodiments, the received patient data set can include disease metrics such as lumbar lordosis, Cobb angles, coronal parameters (e.g., coronal balance, global coronal balance, coronal pelvic tilt, etc.), sagittal parameters (e.g., pelvic incidence, sacral slope, thoracic kyphosis, etc.) and/or pelvic parameters. The disease metrics can include micro-measurements (e.g., metrics associated with specific or individual segments of the patient's spine) and/or macro-measurements (e.g., metrics associated with multiple segments of the patient's spine). In some embodiments, the disease metrics are not included in the patient data set, and the method 500 includes determining (e.g., automatically determining) one or more of the disease metrics based on the patient image data, as described below.

Once the patient data set is received in step 502, the method 500 can continue in step 503 by creating a virtual model of the patient's native anatomical configuration (also referred to as "pre-operative anatomical configuration"). The virtual model can be based on the image data included in the patient data set received in step 502. For example, the same computing system that received the patient data set in step 502 can analyze the image data in the patient data set to generate a virtual model of the patient's native anatomical configuration. The virtual model can be a two- or three-dimensional visual representation of the patient's native anatomy. The virtual model can include one or more regions of interest, and may include some or all of the patient's anatomy within the regions of interest (e.g., any combination of tissue types including, but not limited to, bony structures, cartilage, soft tissue, vascular tissue, nervous tissue, etc.). As a non-limiting example, the virtual model can include a visual representation of the patient's spinal cord region, including some or all of the sacrum, lumbar region, thoracic region, and/or cervical region. In some embodiments, the virtual model includes soft tissue, cartilage, and other non-bony structures. In other embodiments, the virtual model only includes the patient's bony structures. An example of a virtual model of the native anatomical configuration is described below with respect to FIGS. 8A and 8B. In some embodiments, the method 500 can optionally omit creating a virtual model of the patient's native anatomy in step 503, and proceed directly from step 502 to step 504.

In some embodiments, the computing system that generated the virtual model in step 502 can also determine (e.g., automatically determine or measure) one or more disease metrics of the patient based on the virtual model. For example, the computing system may analyze the virtual model to determine the patient's pre-operative lumbar lordosis, Cobb angles, coronal parameters (e.g., coronal balance, global coronal balance, coronal pelvic tilt, etc.), sagittal parameters (e.g., pelvic incidence, sacral slope, thoracic kyphosis, etc.) and/or pelvic parameters. The disease metrics can include micro-measurements (e.g., metrics associated with specific or individual segments of the patient's spine) and/or macro-measurements (e.g., metrics associated with multiple segments of the patient's spine).

The method 500 can continue in step 504 by creating a virtual model of a corrected anatomical configuration (which can also be referred to herein as the "planned configuration," "optimized geometry," "post-operative anatomical configuration," or "target outcome") for the patient. For example, the computing system can, using the analysis procedures described previously, determine a "corrected" or "optimized" anatomical configuration for the particular patient that represents an ideal surgical outcome for the particular patient. This can be done, for example, by analyzing a plurality of reference patient data sets to identify post-operative anatomical configurations for similar patients who had a favorable post-operative outcome, as previously described in detail with respect to FIGS. 1-4C (e.g., based on similarity of the reference patient data set to the patient data set and/or whether the reference patient had a favorable treatment outcome). This may also include applying one or more mathematical rules defining optimal anatomical outcomes (e.g., positional relationships between anatomic elements) and/or target (e.g., acceptable) post-operative metrics/design criteria (e.g., adjust anatomy so that the post-operative sagittal vertical axis is less than 7 mm, the post-operative Cobb angle less than 10 degrees, etc.). Target post-operative metrics can include, but are not limited to, target coronal parameters, target sagittal parameters, target pelvic incidence angle, target Cobb angle, target shoulder tilt, target iliolumbar angle, target coronal balance, target Cobb angle, target lordosis angle, and/or a target intervertebral space height. The different between the native anatomical configuration and the corrected anatomical configuration may be referred to as a "patient-specific correction" or "target correction."

Once the corrected anatomical configuration is determined, the computing system can generate a two- or three-dimensional visual representation of the patient's anatomy with the corrected anatomical configuration. As with the virtual model created in step 503, the virtual model of the patient's corrected anatomical configuration can include one or more regions of interest, and may include some or all of the patient's anatomy within the regions of interest (e.g., any combination of tissue types including, but not limited to, bony structures, cartilage, soft tissue, vascular tissue, nervous tissue, etc.). As a non-limiting example, the virtual model can include a visual representation of the patient's spinal cord region in a corrected anatomical configuration, including some or all of the sacrum, lumbar region, thoracic region, and/or cervical region. In some embodiments, the virtual model includes soft tissue, cartilage, and other non-bony structures. In other embodiments, the virtual model only includes the patient's bony structures. An example of a virtual model of the native anatomical configuration is described below with respect to FIGS. 9A-1-9B-2.

The method 500 can continue in step 506 by generating (e.g., automatically generating) a surgical plan for achieving the corrected anatomical configuration shown by the virtual model. The surgical plan can include pre-operative plans, operative plans, post-operative plans, and/or specific spine metrics associated with the optimal surgical outcome. For example, the surgical plans can include a specific surgical procedure for achieving the corrected anatomical configuration. In the context of spinal surgery, the surgical plan may include a specific fusion surgery (e.g., PLIF, ALIF, TLIF, LLIF, DLIF, XLIF, etc.) across a specific range of vertebral levels (e.g., L1-L4, L1-5, L3-T12, etc.). Of course, other surgical procedures may be identified for achieving the corrected anatomical configuration, such as non-fusion surgical approaches and orthopedic procedures for other areas of the patient. The surgical plan may also include one or more expected spine metrics (e.g., lumbar lordosis, Cobb angles, coronal parameters, sagittal parameters, and/or pelvic parameters) corresponding to the expected post-operative patient anatomy. The surgical plan can be generated by the same or different computing system that created the virtual model of the corrected anatomical configuration. In some embodiments, the surgical plan can also be based on one or more reference patient data sets as previously described with respect to FIGS. 1-4C. In some embodiments, the surgical plan can also be based at least in part on surgeon-specific preferences and/or outcomes associated with a specific surgeon performing the surgery. In some embodiments, more than one surgical plan is generated in step 506 to provide a surgeon with multiple options. An example of a surgical plan is described below with respect to FIG. 10.

After the virtual model of the corrected anatomical configuration is created in step 504 and the surgical plan is generated in step 506, the method 500 can continue in step 508 by transmitting the virtual model of the corrected anatomical configuration and the surgical plan for surgeon review. In some embodiments, the virtual model and the surgical plan are transmitted as a surgical plan report, an example of which is described with respect to FIG. 11. In some embodiments, the same computing system used in steps 502-506 can transmit the virtual model and surgical plan to a computing device for surgeon review (e.g., the client computing device 102 described in FIG. 1 or the computing device 602 described below with respect to FIG. 6). This can include directly transmitting the virtual model and the surgical plan to the computing device or uploading the virtual model and the surgical plan to a cloud or other storage system for subsequent downloading. Although step 508 describes transmitting the surgical plan and the virtual model to the surgeon, one skilled in the art will appreciate from the disclosure herein that images of the virtual model may be included in the surgical plan transmitted to the surgeon, and that the actual model need not be included (e.g., to decrease the file size being transmitted). Additionally, the information transmitted to the surgeon in step 508 may include the virtual model of the patient's native anatomical configuration (or images thereof) in addition to the virtual model of the corrected anatomical configuration. In embodiments in which more than one surgical plan is generated in step 506, the method 500 can include transmitting more than one surgical plan to the surgeon for review and selection.

The surgeon can review the virtual model and surgical plan and, in step 510, either approve or reject the surgical plan (or, if more than one surgical plan is provided in step 508, select one of the provided surgical plans). If the surgeon does not approve the surgical plan in step 510, the surgeon can optionally provide feedback and/or suggested modifications to the surgical plan (e.g., by adjusting the virtual model or changing one or more aspects about the plan). Accordingly, the method 500 can include receiving (e.g., via the computing system) the surgeon feedback and/or suggested modifications. If surgeon feedback and/or suggested modifications are received in step 512, the method 500 can continue in step 514 by revising (e.g., automatically revising via the computing system) the virtual model and/or surgical plan based at least in part on the surgeon feedback and/or suggested modifications received in step 512. In some embodiments, the surgeon does not provide feedback and/or suggested modifications if they reject the surgical plan. In such embodiments, step 512 can be omitted, and the method 500 can continue in step 514 by revising (e.g., automatically revising via the computing system) the virtual model and/or the surgical plan by selecting new and/or additional reference patient data sets. The revised virtual model and/or surgical plan can then be transmitted to the surgeon for review. Steps 508, 510, 512, and 514 can be repeated as many times as necessary until the surgeon approves the surgical plan. Although described as the surgeon reviewing, modifying, approving, and/or rejecting the surgical plan, in some embodiments the surgeon can also review, modify, approve, and/or reject the corrected anatomical configuration shown via the virtual model.

Once surgeon approval of the surgical plan is received in step 510, the method 500 can continue in step 516 by designing (e.g., via the same computing system that performed steps 502-514) a patient-specific implant based on the corrected anatomical configuration and the surgical plan. For example, the patient-specific implant can be specifically designed such that, when it is implanted in the particular patient, it directs the patient's anatomy to occupy the corrected anatomical configuration (e.g., transforming the patient's anatomy from the native anatomical configuration to the corrected anatomical configuration). The patient-specific implant can be designed such that, when implanted, it causes the patient's anatomy to occupy the corrected anatomical configuration for the expected service life of the implant (e.g., 5 years or more, 10 years or more, 20 years or more, 50 years or more, etc.). In some embodiments, the patient-specific implant is designed solely based on the virtual model of the corrected anatomical configuration and/or without reference to pre-operative patient images.

The patient-specific implant can be any of the implants described herein or in any patent references incorporated by reference herein. For example, the patient-specific implant can include one or more of screws (e.g., bone screws, spinal screws, pedicle screws, facet screws), interbody implant devices (e.g., intervertebral implants), cages, plates, rods, discs, fusion devices, spacers, rods, expandable devices, stents, brackets, ties, scaffolds, fixation device, anchors, nuts, bolts, rivets, connectors, tethers, fasteners, joint replacements (e.g., artificial discs), hip implants, or the like. A patient-specific implant design can include data representing one or more of physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties) of the implant. For example, a design for an orthopedic implant can include implant shape, size, material, and/or effective stiffness (e.g., lattice density, number of struts, location of struts, etc.). An example of a patient-specific implant designed via the method 500 is described below with respect to FIGS. 12A and 12B.

In some embodiments, designing the implant in step 516 can optionally include generating fabrication instructions for manufacturing the implant. For example, the computing system may generate computer-executable fabrication instructions that that, when executed by a manufacturing system, cause the manufacturing system to manufacture the implant.

In some embodiments, the patient-specific implant is designed in step 516 only after the surgeon has reviewed and approved the virtual model with the corrected anatomical configuration and the surgical plan. Accordingly, in some embodiments, the implant design is neither transmitted to the surgeon with the surgical plan in step 508, nor manufactured before receiving surgeon approval of the surgical plan. Without being bound by theory, waiting to design the patient-specific implant until after the surgeon approves the surgical plan may increase the efficiency of the method 500 and/or reduce the resources necessary to perform the method 500.

The method 500 can continue in step 518 by manufacturing the patient-specific implant. The implant can be manufactured using additive manufacturing techniques, such as 3D printing, stereolithography, digital light processing, fused deposition modeling, selective laser sintering, selective laser melting, electronic beam melting, laminated object manufacturing, powder bed printing, thermoplastic printing, direct material deposition, or inkjet photo resin printing, or like technologies, or combination thereof. Alternatively or additionally, the implant can be manufactured using subtractive manufacturing techniques, such as CNC machining, electrical discharge machining (EDM), grinding, laser cutting, water jet machining, manual machining (e.g., milling, lathe/turning), or like technologies, or combinations thereof. The implant may be manufactured by any suitable manufacturing system (e.g., the manufacturing system 124 shown in FIG. 1 or the manufacturing system 630 described below with respect to FIG. 6). In some embodiments, the implant is manufactured by the manufacturing system executing the computer-readable fabrication instructions generated by the computing system in step 516.

Once the implant is manufactured in step 518, the method 500 can continue in step 520 by implanting the patient-specific implant into the patient. The surgical procedure can be performed manually, by a robotic surgical platform (e.g., a surgical robot), or a combination thereof. In embodiments in which the surgical procedure is performed at least in part by a robotic surgical platform, the surgical plan can include computer-readable control instructions configured to cause the surgical robot to perform, at least partly, the patient-specific surgical procedure. Additional details regarding a robotic surgical platform are described below with respect to FIG. 6.

The method 500 can be implemented and performed in various ways. In some embodiments, steps 502-516 can be performed by a computing system (e.g., the computing system 606 described below with respect to FIG. 6) associated with a first entity, step 518 can be performed by a manufacturing system associated with a second entity, and step 520 can be performed by a surgical provider, surgeon, and/or robotic surgical platform associated with a third entity. Any of the foregoing steps may also be implemented as computer-readable instructions stored in memory and executable by one or more processors of the associated computing system(s).

Figure 6:
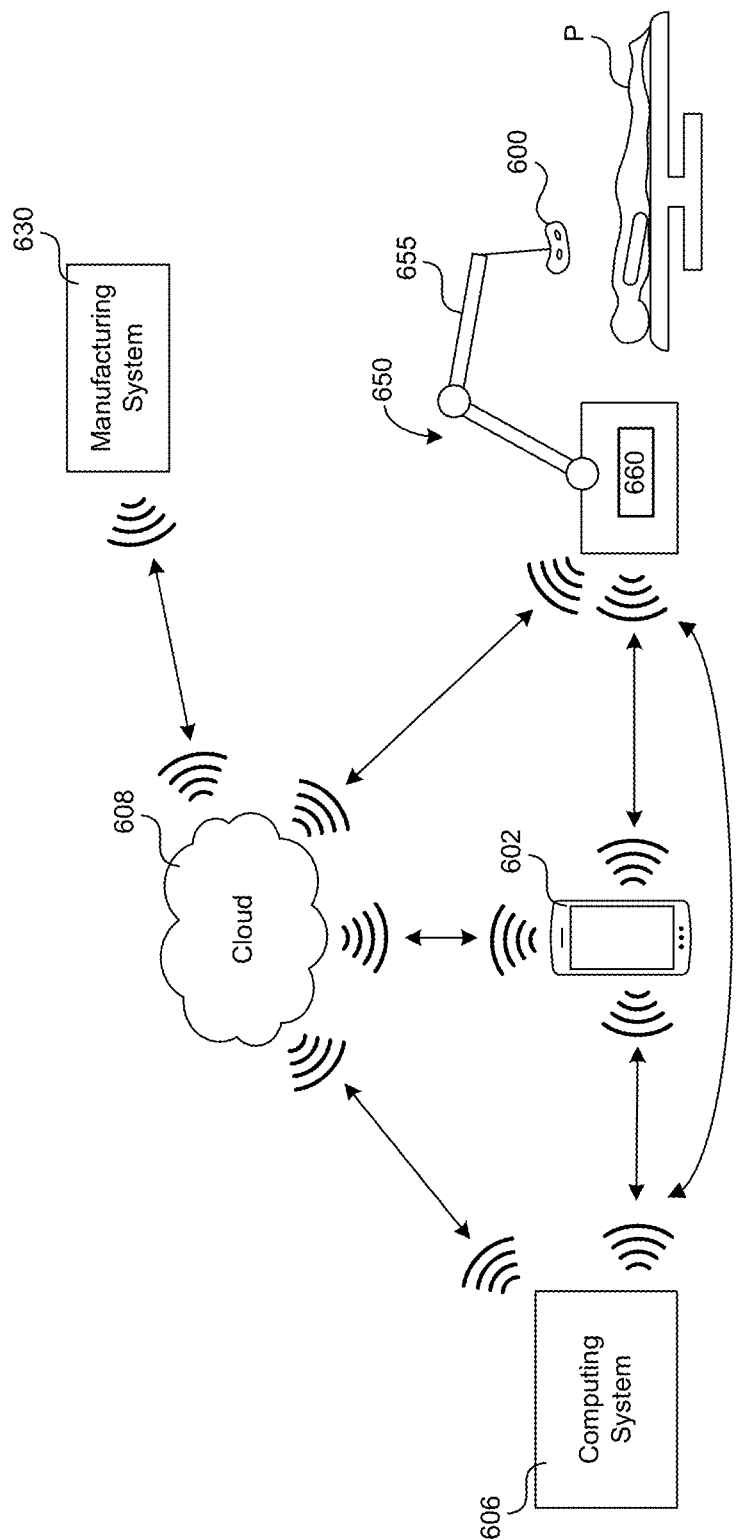
FIG. 6 is a partially schematic illustration of an operative setup and associated computing systems for providing patient-specific medical care, according to an embodiment.
Figure 7D:
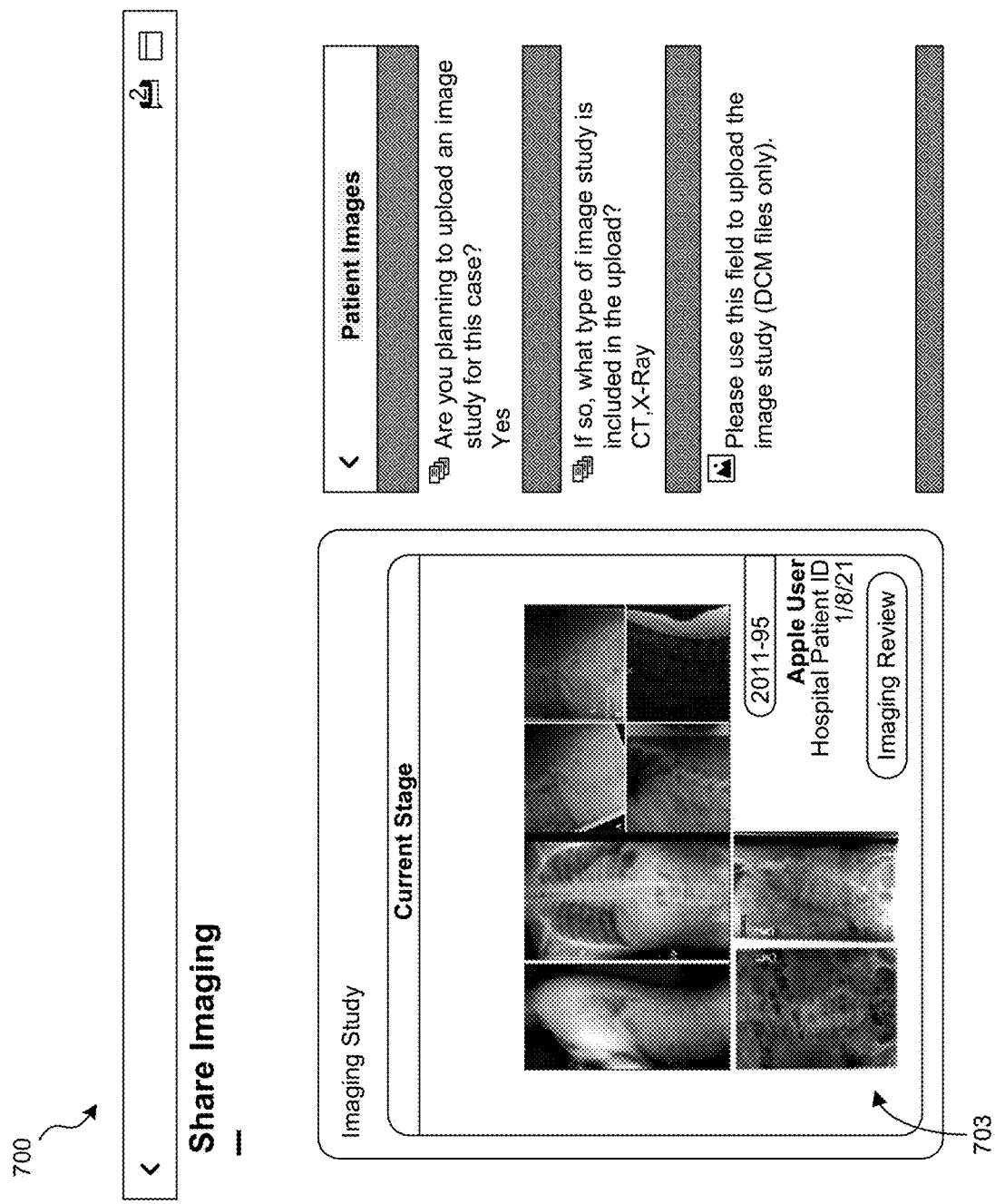

FIG. 6 is a schematic illustration of an operative setup including select systems and devices that can be used to provide patient-specific medical care, such as for performing the method 500 described with respect to FIG. 5. As shown, the operative setup includes a computing device 602, a computing system 606, a cloud 608, a manufacturing system 630, and a robotic surgical platform 650. The computing device 602 can be a user device, such as a smart phone, mobile device, laptop, desktop, personal computer, tablet, phablet, or other such devices known in the art. In operation, a user (e.g., a surgeon) can collect, retrieve, review, modify, or otherwise interact with a patient data set using the computing device 602. The computing system 606 can include any suitable computing system configured to store one or more software modules for identifying reference patient data sets, determining patient-specific surgical plans, generating virtual models of patient anatomy, designing patient-specific implants, or the like. The one or more software modules can include algorithms, machine-learning models, artificial intelligence architectures, or the like for performing select operations. The cloud 608 can be any suitable network and/or storage system, and may include any combination of hardware and/or virtual computing resources. The manufacturing system 630 can be any suitable manufacturing system for producing patient-specific implants, including any of those previously described herein. The robotic surgical platform 650 (referred to herein as "the platform 650") can be configured to perform or otherwise assist with one or more aspects of a surgical procedure.

In a representative operation, the computing device 602, the computing system 606, the cloud 608, the manufacturing system 630, and the platform 650 can be used to provide patient-specific medical care, such as to perform the method 500 described with respect to FIG. 5. For example, the computing system 606 can receive a patient data set from the computing device 602 (e.g., step 502 of the method 500). In some embodiments, the computing device 602 can directly transmit the patient data set to the computing system 606. In other embodiments, the computing device 602 can upload the patient data set into the cloud 608, and the computing system 606 can download or otherwise access the patient data set from the cloud. Once the computing system 606 receives the patient data set, the computing system 606 can create a virtual model of the patient's native anatomical configuration (e.g., step 503 of the method 500), create a virtual model of the corrected anatomical configuration (e.g., step 504 of the method 500), and/or generate a surgical plan for achieving the corrected anatomical configuration (e.g., step 506 of the method 500). The computing system can perform the foregoing operations via the one or more software modules, which in some embodiments include machine learning models or other artificial intelligence architectures. Once the virtual models and the surgical plan are created, the computing system 606 can transmit the virtual models and the surgical plan to the surgeon for review (e.g., step 508 of the method 500). This can include, for example, directly transmitting the virtual models and the surgical plan to the computing device 602 for surgeon review. In other embodiments, this can include uploading the virtual models and the surgical plan to the cloud 608. A surgeon can then download or otherwise access the virtual models and the surgical plan from the cloud 608 using the computing device 602.

The surgeon can use the computing device 602 to review the virtual models and the surgical plan. The surgeon can also approve or reject the surgical plan and provide any feedback regarding the surgical plan using the computing device 602. The surgeon's approval, rejection, and/or feedback regarding the surgical plan can be transmitted to, and received by, the computing system 606 (e.g., steps 510 and 512 of the method 500). The computing system 606 can than revise the virtual model and/or the surgical plan (e.g., step 514 of the method 500). The computing system 606 can transmit the revised virtual model and surgical plan to the surgeon for review (e.g., by uploading it to the cloud 608 or directly transmitting it to the computing device 602).

The computing system 606 can also design the patient-specific implant based on the corrected anatomical configuration and the surgical plan (e.g., step 516 of the method 500) using, the one or more software modules. In some embodiments, software modules rely on one or more algorithms, machine learning models, or other artificial intelligence architectures to design the implant. Once the computing system 606 designs the patient-specific implant, the computing system 606 can upload the design and/or manufacturing instructions to the cloud 608. The computing system 606 may also create fabrication instructions (e.g., computer-readable fabrication instructions) for manufacturing the patient-specific implant. In such embodiments, the computing system 606 can upload the fabrication instructions to the cloud 608.

The manufacturing system 630 can download or otherwise access the design and/or fabrication instructions for the patient-specific implant from the cloud 608. The manufacturing system can then manufacture the patient-specific implant (e.g., step 518 in the method 500) using additive manufacturing techniques, subtractive manufacturing techniques, or other suitable manufacturing techniques.

The robotic surgical platform 650 can perform or otherwise assist with one or more aspects of the surgical procedure (e.g., step 520 of the method 500). For example, the platform 650 can prepare tissue for an incision, make an incision, make a resection, remove tissue, manipulate tissue, perform a corrective maneuver, deliver the implant to a target site, deploy the implant at the target site, adjust the implant at the target site, manipulate the implant once it is implanted, secure the implant at the target site, explant the implant, suture tissue, etc. The platform 650 can therefore include one or more arms 655 and end effectors for holding various surgical tools (e.g., graspers, clips, needles, needle drivers, irrigation tools, suction tools, staplers, screw driver assemblies, etc.), imaging instruments (e.g., cameras, sensors, etc.), and/or medical devices (e.g., the implant 600) and that enable the platform 650 to perform the one or more aspects of the surgical plan. Although shown as having one arm 655, one skilled in the art will appreciate that the platform 650 can have a plurality of arms (e.g., two, three, four, or more) and any number of joints, linkages, motors, and degrees of freedom. In some embodiments, the platform 650 may have a first arm dedicated to holding one or more imaging instruments, while the remainder of the arms hold various surgical tools. In some embodiments, the tools can be releasably secured to the arms such that they can be selectively interchanged before, during, or after an operative procedure. The arms can be moveable through a variety of ranges of motion (e.g., degrees of freedom) to provide adequate dexterity for performing various aspects of the operative procedure.

The platform 650 can include a control module 660 for controlling operation of the arm(s) 655. In some embodiments, the control module 660 includes a user input device (not shown) for controlling operation of the arm(s) 655. The user input device can be a joystick, a mouse, a keyboard, a touchscreen, an infrared sensor, a touchpad, a wearable input device, a camera- or image-based input device, a microphone, or other user input devices. A user (e.g., a surgeon) can interact with the user input device to control movement of the arm(s) 655.

In some embodiments, the control module 660 includes one or more processors for executing machine-readable operative instructions that, when executed, automatically control operation of the arm 655 to perform one or more aspects of the surgical procedure. In some embodiments, the control module 660 may receive the machine-readable operative instructions (e.g., from the cloud 608) specifying one or more steps of the surgical procedure that, when executed by the control module 660, cause the platform 650 to perform the one or more steps of the surgical procedure. For example, the machine-readable operative instructions may direct the platform 650 to prepare tissue for an incision, make an incision, make a resection, remove tissue, manipulate tissue, perform a corrective maneuver, deliver the implant 600 to a target site, deploy the implant 600 at the target site, adjust a configuration of the implant 600 at the target site, manipulate the implant 600 once it is implanted, secure the implant 600 at the target site, explant the implant 600, suture tissue, and the like. The operative instructions may therefor include particular instructions for articulating the arm 655 to perform or otherwise aid in the delivery of the patient-specific implant.

In some embodiments, the platform 650 can generate (e.g., as opposed to simply receiving) the machine-readable operative instructions based on the surgical plan. For example, the surgical plan can include information about the delivery path, tools, and implantation site. The platform 650 can analyze the surgical plan and develop executable operative instructions for performing the patient-specific procedure based on the capabilities (e.g., configuration and number of robotic arms, functionality of and effectors, guidance systems, visualization systems, etc.) of the robotic system.

This enables the operative setup shown in FIG. 6 to be compatible with a wide range of different types of robotic surgery systems.

The platform 650 can include one or more communication devices (e.g., components having VLC, WiMAX, LTE, WLAN, IR communication, PSTN, Radio waves, Bluetooth, and/or Wi-Fi operability) for establishing a connection with the cloud 608 and/or the computing device 602 for accessing and/or downloading the surgical plan and/or the machine-readable operative instructions. For example, the cloud 608 can receive a request for a particular surgical plan from the platform 650 and send the plan to the platform 650. Once identified, the cloud 608 can transmit the surgical plan directly to the platform 650 for execution. In some embodiments, the cloud 608 can transmit the surgical plan to one or more intermediate networked devices (e.g., the computing device 602) rather than transmitting the surgical plan directly to the platform 650. A user can review the surgical plan using the computing device 602 before transmitting the surgical plan to the platform 650 for execution. Additional details for identifying, storing, downloading, and accessing patient-specific surgical plans are described in U.S. application Ser. No. 16/990,810, filed Aug. 11, 2020, the disclosure of which is incorporated by reference herein in its entirety.

The platform 650 can include additional components not expressly shown in FIG. 6. For example, in various embodiments the platform 650 may include one or more displays (e.g., LCD display screen, an LED display screen, a projected, holographic, or augmented reality display (e.g., a heads-up display device or a head-mounted device), one or more I/O devices (e.g., a network card, video card, audio card, USB, firewire or other external device, camera, printer, speakers, CD-ROM drive, DVD drive, disk drive, or Blu-Ray device), and/or a memory (e.g., random access memory (RAM), various caches, CPU registers, read-only memory (ROM), and writable non-volatile memory, such as flash memory, hard drives, floppy disks, CDs, DVDs, magnetic storage devices, tape drives, device buffers, and so forth). In some embodiments, the foregoing components can be generally similar to the like components described in detail with respect to computing device 200 in FIG. 2.

Without being bound by theory, using a robotic surgical platform to perform various aspects of the surgical plans described herein is expected to provide several advantages over conventional operative techniques. For example, use of robotic surgical platforms may improve surgical outcomes and/or shorten recovery times by, for example, decreasing incision size, decreasing blood loss, decreasing a length of time of the operative procedure, increasing the accuracy and precision of the surgery (e.g., the placement of the implant at the target location), and the like. The platform 650 can also avoid or reduce user input errors, e.g., by including one or more scanners for obtaining information from instruments (e.g., instruments with retrieval features), tools, the patient specific implant 600 (e.g., after the implant 600 has been gripped by the arm 655), etc. The platform 650 can confirm use of proper instruments prior and during the surgical procedure. If the platform 650 identifies an incorrect instrument or tool, an alert can be sent to a user that another instrument or tool should be installed. The user can scan the new instrument to confirm that the instrument is appropriate for the surgical plan. In some embodiments, the surgical plan includes instructions for use, a list of instruments, instrument specifications, replacement instruments, and the like. The platform 650 can perform pre- and post-surgical checking routines based on information from the scanners.

FIGS. 7A-13 further illustrate select aspects of providing patient-specific medical care, e.g., in accordance with the method 500. For example, FIG. 7A-7D illustrate an example of a patient data set 700 (e.g., as received in step 502 of the method 500). The patient data set 700 can include any of the information previously described with respect to the patient data set. For example, the patient data set 700 includes patient information 701 (e.g., patient identification no., patient MRN, patient name, sex, age, body mass index (BMI), surgery date, surgeon, etc., shown in FIGS. 7A and 7B), diagnostic information 702 (e.g., Oswestry Disability Index (ODI), VAS-back score, VAS-leg score, Pre-operative pelvic incidence, pre-operative lumbar lordosis, pre-operative PI-LL angel, pre-operative lumbar coronal cobb, etc., shown in FIGS. 7B and 7C), and image data 703 (x-ray, CT, MRI, etc., shown in FIG. 7D). In the illustrated embodiment, the patient data set 700 is collected by a healthcare provider (e.g., a surgeon, a nurse, etc.) using a digital and/or fillable report that can be accessed using a computing device (e.g., the computing device 602 shown in FIG. 6). In some embodiments, the patient data set 700 can be automatically or at least partially automatically generated based on digital medical records of the patient. Regardless, once collected, the patient data set 700 can be transmitted to the computing system configured to generate the surgical plan for the patient (e.g., the computing system 606 shown in FIG. 6).

Figure 8A:
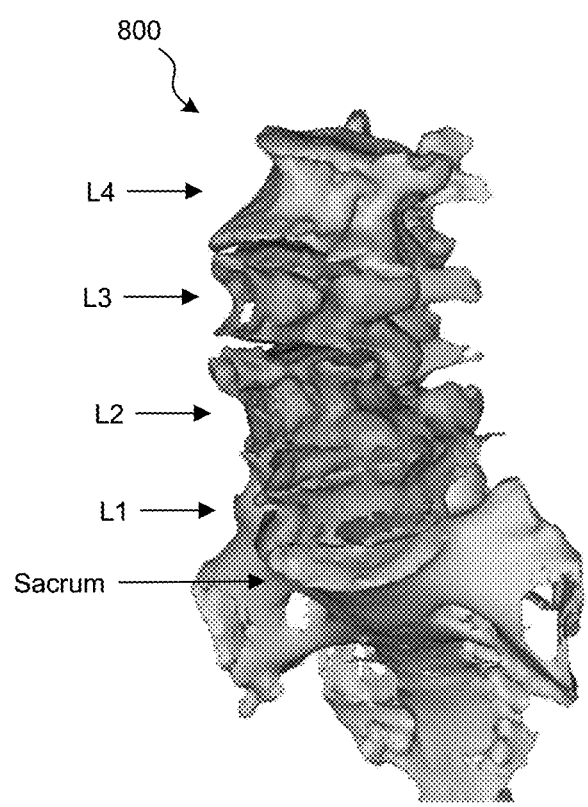
FIGS. 8A and 8B illustrate an exemplary virtual model of a patient's spine that may be used and/or generated in connection with the methods described herein, according to an embodiment.
Figure 8B:
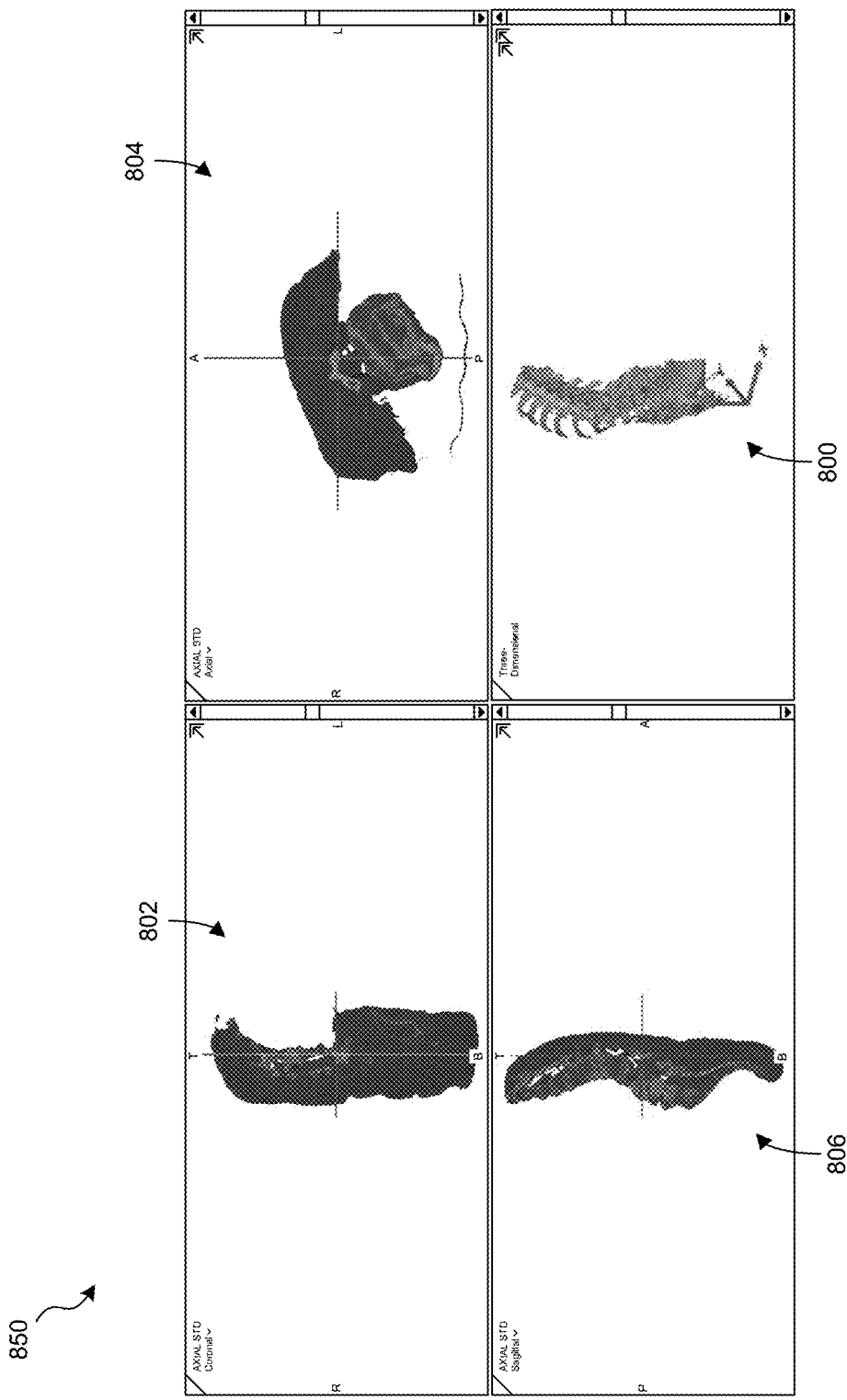

FIGS. 8A and 8B illustrate an example of a virtual model 800 of a patient's native anatomical configuration (e.g., as created in step 503 of the method 500). In particular, FIG. 8A is an enlarged view of the virtual model 800 of the patient's native anatomy and shows the patient's native anatomy of their lower spinal cord region. The virtual model 800 is a three-dimensional visual representation of the patient's native anatomy. In the illustrated embodiment, the virtual model includes a portion of the spinal column extending from the sacrum to the L4 vertebral level. Of course, the virtual model can include other regions of the patient's spinal column, including cervical vertebrae, thoracic vertebrae, lumbar vertebrae, and the sacrum. The illustrated virtual model 800 only includes bony structures of the patient's anatomy, but in other embodiments may include additional structures, such as cartilage, soft tissue, vascular tissue, nervous tissue, etc.

FIG. 8B illustrates a virtual model display 850 (referred to herein as the "display 850") showing different views of the virtual model 800. The virtual model display 850 includes a three-dimensional view of the virtual model 800, one or more coronal cross-section(s) 802 of the virtual model 800, one or more axial cross section(s) 804 of the virtual model 800, and/or one or more sagittal cross-section (s) 806 of the virtual model 800. Of course, other views are possible and can be included on the virtual model display 850. In some embodiments, the virtual model 800 may be interactive such that a user can manipulate the orientation or view of the virtual model 800 (e.g., rotate), change the depth of the displayed cross-sections, select and isolate specific bony structures, or the like.

Figures 2, 9A:
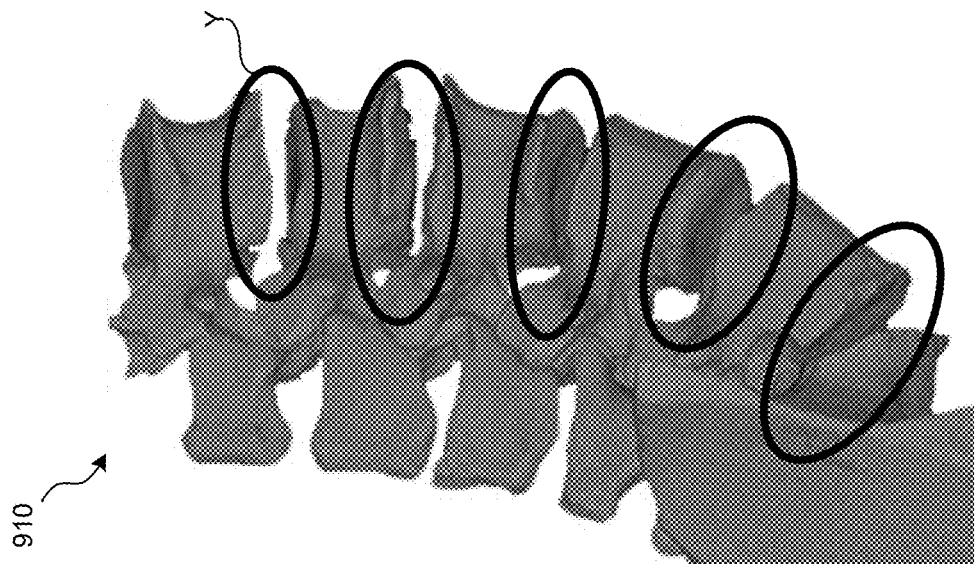
Figures 1, 9A:
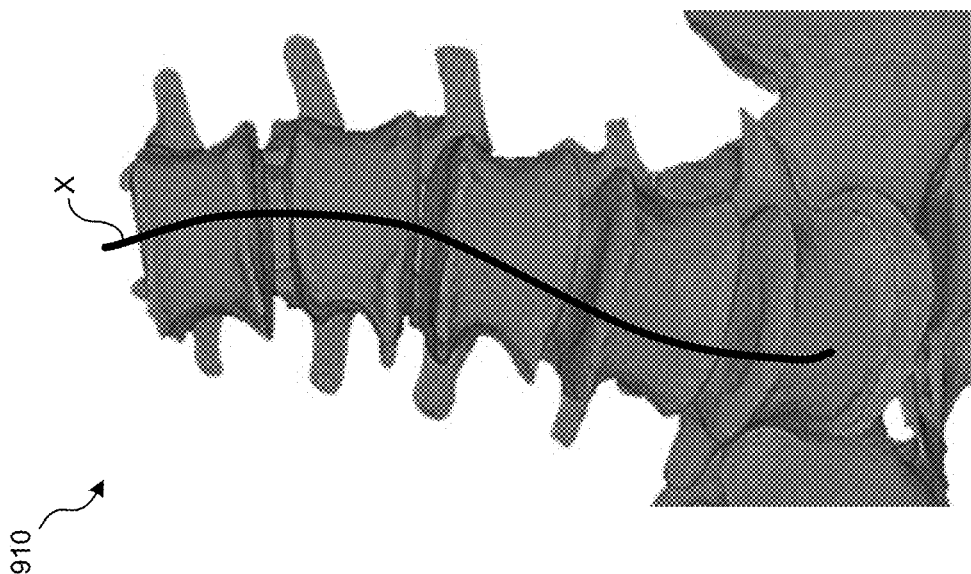
Figures 1, 2, 9B:
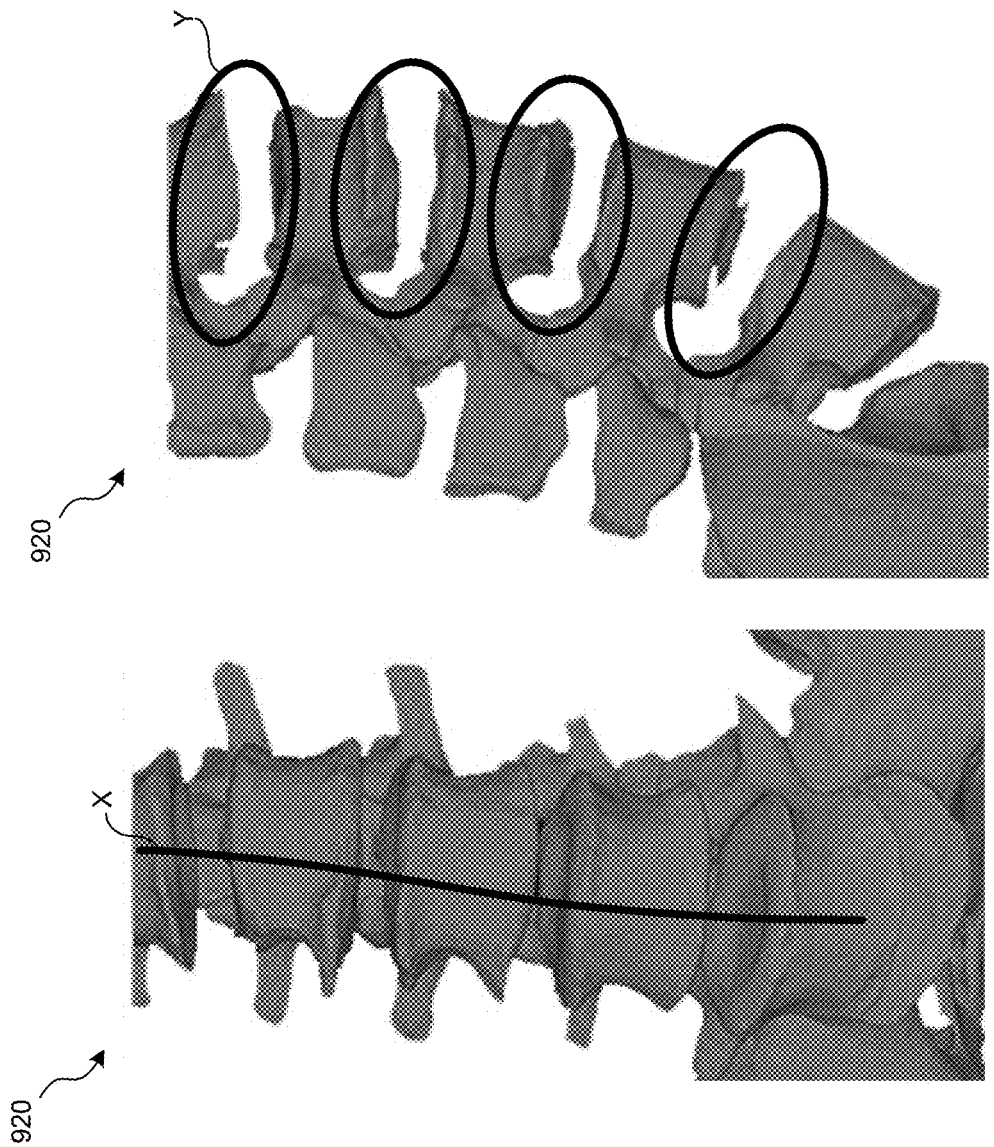

FIGS. 9A-1-9B-2 demonstrate an example of a virtual model of a patient's native anatomical configuration (e.g., as created in step 503 of the method 500) and a virtual model of the patient's corrected anatomical configuration (e.g., as created in step 504 of the method 500). In particular, FIGS. 9A-1 and 9A-2 are anterior and lateral views, respectively, of a virtual model 910 showing a native anatomical configuration of a patient, and FIGS. 9B-1 and 9B-2 are anterior and lateral views, respectively, of a virtual model 920 showing the corrected anatomical configuration for the same patient. Referring first to FIG. 9A-1, the anterior view of the virtual model 910 illustrates the patient has abnormal curvature (e.g., scoliosis) of their spinal column. This is marked by line X, which follows a rostral-caudal axis of the spinal column. Referring next to FIG. 9A-1, the lateral view of the virtual model 910 illustrates the patient has collapsed discs or decreased spacing between adjacent vertebral endplates, marked by ovals Y. FIGS. 9B-1 and 9B-2 illustrate the corrected virtual model 920 accounting for the abnormal anatomical configurations shown in FIGS. 9A-1 and 9A-2. For example, FIG. 9B-1, which is an anterior view of the virtual model 920, illustrates the patient's spinal column having corrected alignment (e.g., the abnormal curvature has been reduced). This correction is shown by line X, which also follows a rostral-caudal axis of the spinal column. FIG. 9B-2, which is a lateral view of the virtual model 920, illustrates the patient's spinal column having restored disc height (e.g., increased spacing between adjacent vertebral endplates), also marked by ovals Y. The lines X and the ovals Y are provided in FIGS. 9A-1-9B-2 to more clearly demonstrate the correction between the virtual models 910 and 920, and are not necessarily included on the virtual models generated in accordance with the present technology.

Figure 10:
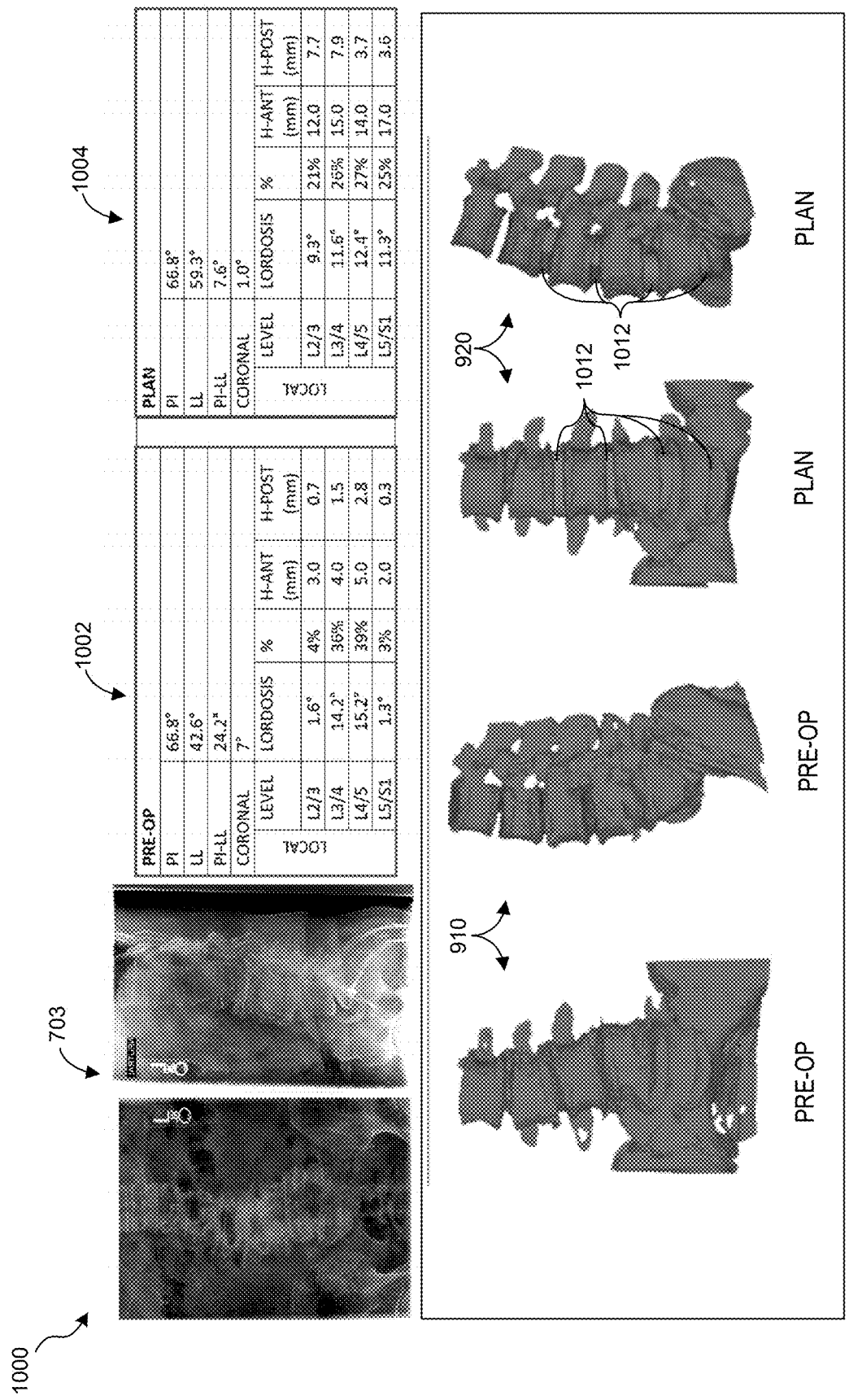
FIG. 10 illustrates an exemplary surgical plan for a patient-specific surgical procedure that may be used and/or generated in connection with the methods described herein, according to an embodiment.

FIG. 10 illustrates an example of a surgical plan 1000 (e.g., as generated in step 506 of the method 500). The surgical plan 1000 can include pre-operative patient metrics 1002, predicted post-operative patient metrics 1004, one or more patient images (e.g., the patient images 703 received as part of the patient data set), the virtual model 910 (which can be the model itself or one or more images derived from the model) of the patient's native anatomical configuration (e.g., pre-operative patient anatomy), and/or the virtual model 920 (which can be the model itself or one or more images derived from the model) of the patient's corrected anatomical configuration (e.g., predicted post-operative patient anatomy). The virtual model 920 of the predicted post-operative patient anatomy can optionally include one or more implants 1012 shown as implanted in the patient's spinal cord region to demonstrate how patient anatomy will look following the surgery. Although four implants 1012 are shown in the virtual model 920, the surgical plan 1000 may include more or fewer implants 1012, including one, two, three, five, six, seven, eight, or more implants 1012.

The surgical plan 1000 can include additional information beyond what is illustrated in FIG. 10. For example, the surgical plan 1000 may include pre-operative instructions, operative instructions, and/or post-operative instructions. Operative instructions can include one or more specific procedures to be performed (e.g., PLIF, ALIF, TLIF, LLIF, DLIF, XLIF, etc.) and/or one or more specific targets of the operation (e.g., fusion of vertebral levels L1-L4, anchoring screw to be inserted in lateral surface of L4, etc.). Although the surgical plan 1000 is demonstrated in FIG. 10 as a visual report, the surgical plan 1000 can also be encoded in computer-executable instructions that, when executed by a processor connected to a computing device, cause the surgical plan 1000 to be displayed by the computing device. In some embodiments, the surgical plan 1000 may also include machine-readable operative instructions for carrying out the surgical plan. For example, the surgical plan can include operative instructions for a robotic surgical platform to carry out one or more steps of the surgical plan 1000.

Figure 11:
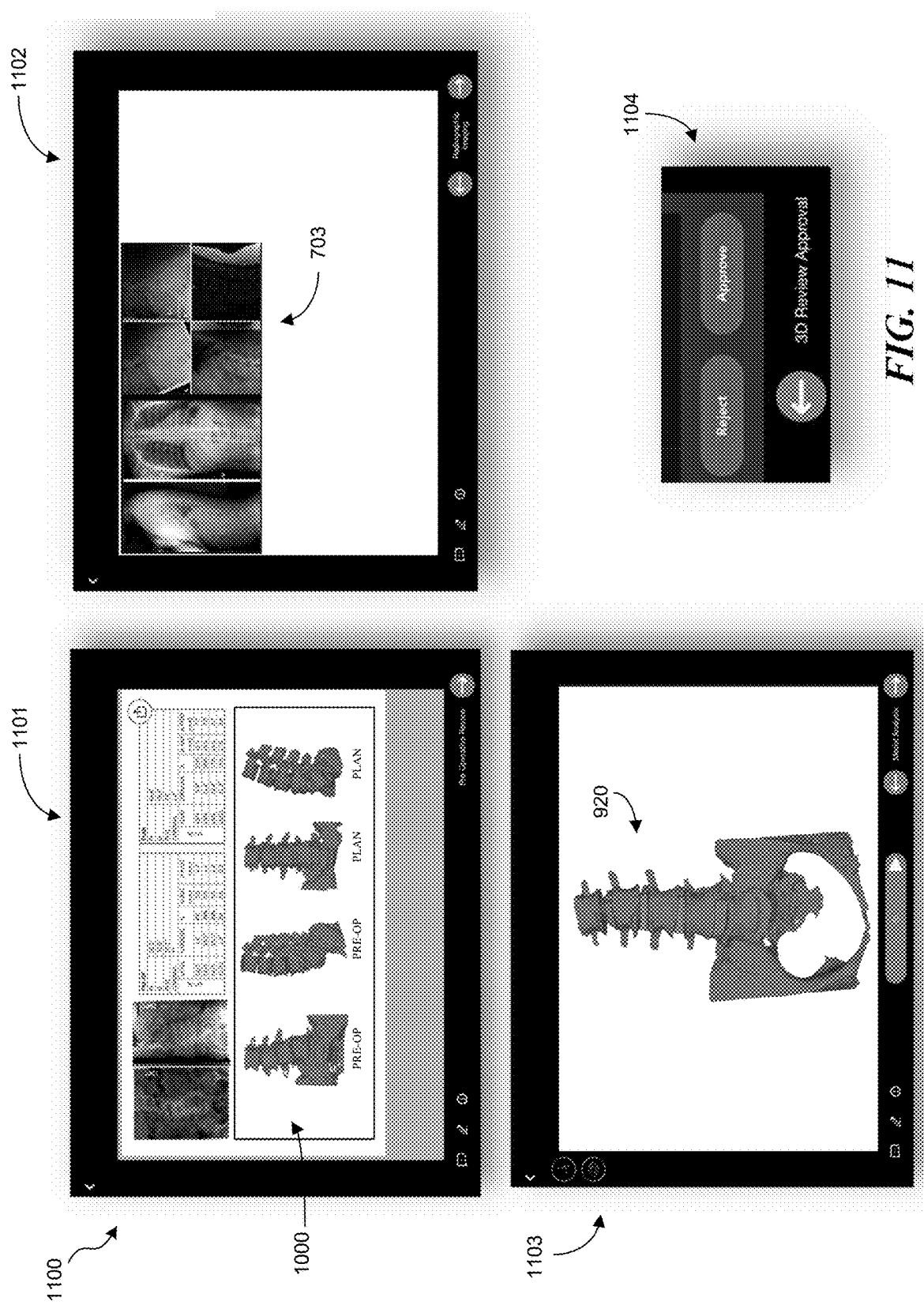
FIG. 11 illustrates an exemplary surgical plan report detailing the surgical plan shown in FIG. 10 for surgeon review and that may be used and/or generated in connection with the methods described herein, according to an embodiment.

FIG. 11 provides a series of images illustrating an example of a patient surgical plan report 1100 that includes the surgical plan 1000 and that may be transmitted to a surgeon for review and approval (e.g., as transmitted in step 508 of the method 500). The surgical plan report 1100 can include a multi-page report detailing aspects of the surgical plan 1000. For example, the multi-page report may include a first page 1101 demonstrating an overview of the surgical plan 1000 (e.g., as shown in FIG. 10), a second page 1102 illustrating patient images (e.g., such as the patient images 703 received in step 502 and shown in FIG. 7D), a third page 1103 illustrating an enlarged view of the virtual model of the corrected anatomical configuration (e.g., the virtual model 920 shown in FIG. 9), and a fourth page 1104 prompting the surgeon to either approve or reject the surgical plan 900. Of course, additional information about the surgical plan can be presented with the report 1100 in the same or different formats. In some embodiments, if the surgeon rejects the surgical plan 1000, the surgeon can be prompted to provide feedback regarding the aspects of the surgical plan 1000 the surgeon would like adjusted.

The patient surgical plan report 1100 can be presented to the surgeon on a digital display of a computing device (e.g., the client computing device 102 shown in FIG. 1 or the computing device 602 shown in FIG. 6). In some embodiments, the report 1100 is interactive and the surgeon can manipulate various aspects of the report 1100 (e.g., adjust views of the virtual model, zoom-in, zoom-out, annotate, etc.). However, even if the report 1100 is interactive, the surgeon generally cannot directly change the surgical plan 1000. Rather, the surgeon may provide feedback and suggested changes to the surgical plan 1000, which can be sent back to the computing system that generated the surgical plan 1000 for analysis and refinement.

Figure 12A:
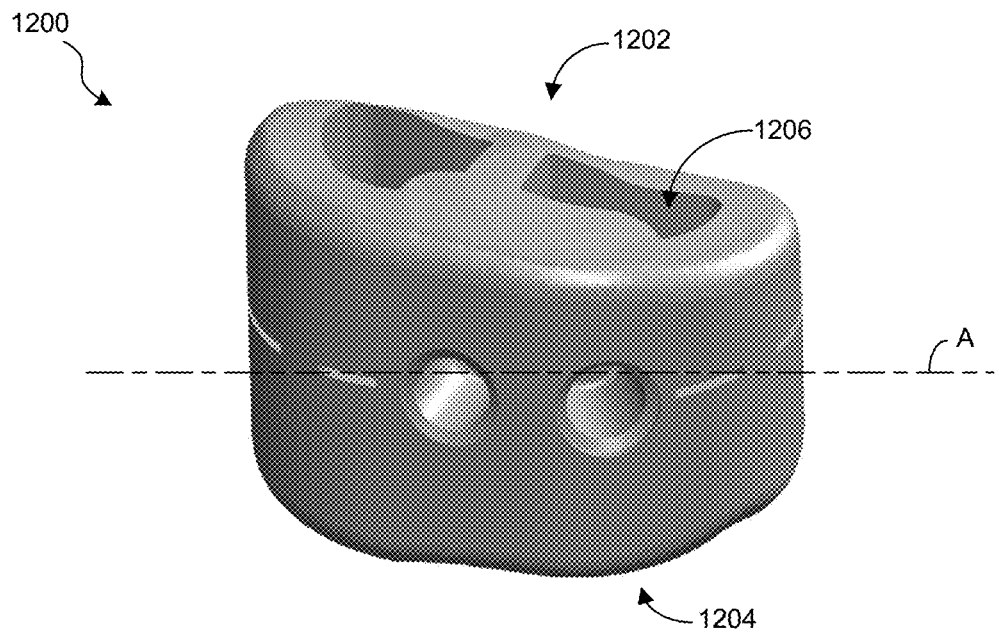
FIGS. 12A and 12B illustrate an exemplary patient-specific implant that can be used and/or generated in connection with the methods described herein, according to an embodiment.
Figure 12B:
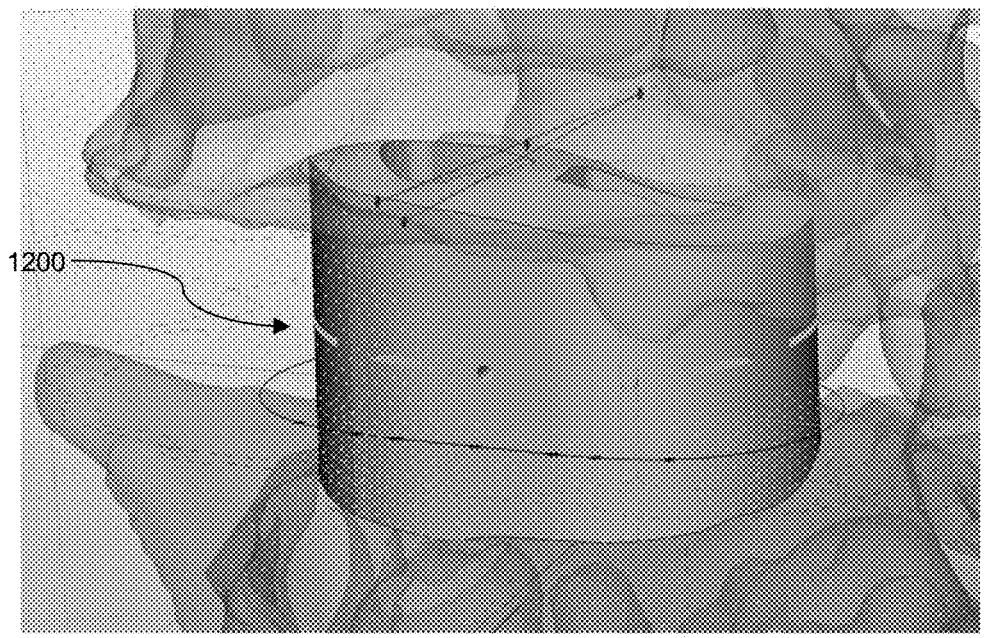

FIG. 12A illustrates an example of a patient-specific implant 1200 (e.g., as designed in step 516 and manufactured in step 518 of the method 500), and FIG. 12B illustrates the implant 1200 implanted in the patient. The implant 1200 can be any orthopedic or other implant specifically designed to induce the patient's body to conform to the previously identified corrected anatomical configuration. In the illustrated embodiment, the implant 1200 is an vertebral interbody device having a first (e.g., upper) surface 1202 configured to engage an inferior endplate surface of a superior vertebral body and a second (e.g., lower) surface 1204 configured to engage a superior endplate surface of an inferior vertebral body. The first surface 1202 can have a patient-specific topography designed to match (e.g., mate with) the topography of the inferior endplate surface of the superior vertebral body to form a generally gapless interface therebetween. Likewise, the second surface 1204 can have a patient-specific topography designed to match or mate with the topography of the superior endplate surface of the inferior vertebral body to form a generally gapless interface therebetween. The implant 1200 may also include a recess 1206 or other feature configured to promote bony ingrowth. Because the implant 1200 is patient-specific and designed to induce a geometric change in the patient, the implant 1200 is not necessarily symmetric, and is often asymmetric. For example, in the illustrated embodiment, the implant 1200 has a non-uniform thickness such that a plane defined by the first surface 1202 is not parallel to a central longitudinal axis A of the implant 1200. Of course, because the implants described herein, including the implant 1200, are patient-specific, the present technology is not limited to any particular implant design or characteristic. Additional features of patient-specific implants that can be designed and manufactured in accordance with the present technology are described in U.S. patents application Ser. No. 16/987,113 and Ser. No. 17/100,396, the disclosures of which are incorporated by reference herein in their entireties.

Figure 13:
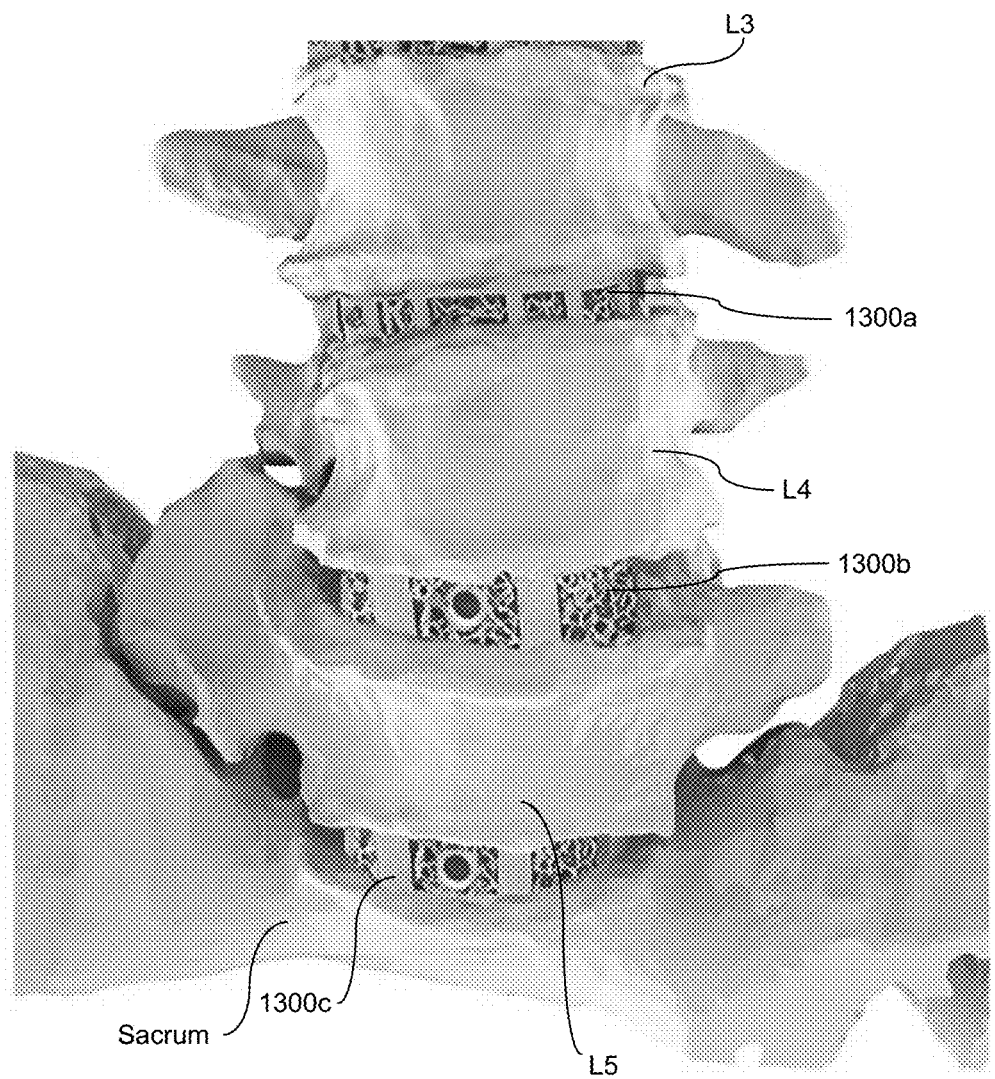
FIG. 13 illustrates a segment of a patient's spine after several patient-specific implants have been implanted therein.

The patient-specific medical procedures described herein can involve implanting more than one patient-specific implant into the patient to achieve the corrected anatomical configuration (e.g., a multi-site procedure). FIG. 13, for example, illustrates a lower spinal cord region having three patient specific implants 1300a-1300c implanted at different vertebral levels. More specifically, a first implant 1300a is implanted between the L3 and L4 vertebral bodies, a second implant 1300b is implanted between the L4 and L5 vertebral bodies, and a third implant 1300c is implanted between the L5 vertebral body and the sacrum. Together, the implants 1300a-c can cause the patient's spinal cord region to assume the previously identified corrected anatomical configuration (e.g., transforming the patient's anatomy from its pre-operative diseased configuration to the post-operative optimized configuration). In some embodiments, more or fewer implants are used to achieve the corrected anatomical configuration. For example, in some embodiments one, two, four, five, six, seven, eight, or more implants are used to achieve the corrected anatomical configuration. In embodiments involving more than one implant, the implants do not necessarily have the same shape, size, or function. In fact, the multiple implants will often have different geometries and topographies to correspond to the target vertebral level at which they will be implanted. As also shown in FIG. 13, the patient-specific medical procedures described herein can involve treating the patient at multiple target regions (e.g., multiple vertebral levels).

In addition to designing patient-specific medical care based off reference patient data sets, the systems and methods of the present technology may also design patient-specific medical care based off disease progression for a particular patient. In some embodiments, the present technology therefore includes software modules (e.g., machine learning models or other algorithms) that can be used to analyze, predict, and/or model disease progression for a particular patient. The machine learning models can be trained based off a plurality of reference patient data sets that includes, in addition to the patient data described with respect to FIG. 1, disease progression metrics for each of the reference patients. The progression metrics can include measurements for disease metrics over a period of time. Suitable metrics may include spinopelvic parameters (e.g., lumbar lordosis, pelvic tilt, sagittal vertical axis (SVA), cobb angel, coronal offset, etc.), disability scores, functional ability scores, flexibility scores, VAS pain scores, or the like. The progression of the metrics for each reference patient can be correlated to other patient information for the specific reference patient (e.g., age, sex, height, weight, activity level, diet, etc.).

In some embodiments, the present technology includes a disease progression module that includes an algorithm, machine learning model, or other software analytical tool for predicting disease progression in a particular patient. The disease progression module can be trained based on reference patient data sets that includes patient information (e.g., age, sex, height, weight, activity level, diet) and disease metrics (e.g., diagnosis, spinopelvic parameters such as lumbar lordosis, pelvic tilt, sagittal vertical axis, cobb angel, coronal offset, etc., disability scores, functional ability scores, flexibility scores, VAS pain scores, etc.). The disease metrics can include values over a period of time. For example, the reference patient data may include values of disease metrics on a daily, weekly, monthly, bi-monthly, yearly, or other basis. By measuring the metrics over a period of time, changes in the values of the metrics can be tracked as an estimate of disease progression and correlated to other patient data.

In some embodiments, the disease progression module can therefore estimate the rate of disease progression for a particular patient. The progression may be estimated by providing estimated changes in one or more disease metrics over a period of time (e.g., X % increase in a disease metric per year). The rate can be constant (e.g., 5% increase in pelvic tilt per year) or variable (e.g., 5% increase in pelvic tilt for a first year, 10% increase in pelvic tilt for a second year, etc.). In some embodiments, the estimated rate of progression can be transmitted to a surgeon or other healthcare provider, who can review and update the estimate, if necessary.

As a non-limiting example, a particular patient who is a fifty-five-year-old male may have a SVA value of 6 mm. The disease progression module can analyze patient reference data sets to identify disease progression for individual reference patients have one or more similarities with the particular patient (e.g., individual patients of the reference patients who have an SVA value of about 6 mm and are approximately the same age, weight, height, and/or sex of the patient). Based on this analysis, the disease progression module can predict the rate of disease progression if no surgical intervention occurs (e.g., the patient's VAS pain scores may increase 5%, 10%, or 15% annually if no surgical intervention occurs, the SVA value may continue to increase by 5% annually if no surgical intervention occurs, etc.).

The systems and methods described herein can also generate models/simulations based on the estimated rates of disease progression, thereby modeling different outcomes over a desired period of times. Additionally, the models/simulations can account for any number of additional diseases or condition to predict the patient's overall health, mobility, or the like. These additional diseases or conditions can, in combination with other patient health factors (e.g., height, weight, age, activity level, etc.) be used to generate a patient health score reflecting the overall health of the patient. The patient health score can be displayed for surgeon review and/or incorporated into the estimation of disease progression. Accordingly, the present technology can generate one or more virtual simulations of the predicted disease progression to demonstrate how the patient's anatomy is predicted to change over time. Physician input can be used to generate or modify the virtual simulation(s). The present technology can generate one or more post-treatment virtual simulations based on the received physician input for review by the healthcare provider, patient, etc.

In some embodiments, the present technology can also predict, model, and/or simulate disease progression based on one or more potential surgical interventions. For example, the disease progression module may simulate what a patient's anatomy may look like 1, 2, 5, or 10 years post-surgery for several surgical intervention options. The simulations may also incorporate non-surgical factors, such as patient age, height, weight, sex, activity level, other health conditions, or the like, as previously described. Based on these simulations, the system and/or a surgeon can select which surgical intervention is best suited for long-term efficacy. These simulations can also be used to determine patient-specific corrections that compensate for the projected diseases progression.

Accordingly, in some embodiments, multiple disease progression models (e.g., two, three, four, five, six, or more) are simulated to provide disease progression data for several different surgical intervention options or other scenarios. For example, the disease progression module can generate models that predict post-surgical disease progression for each of three different surgical interventions. A surgeon or other healthcare provider can review the disease progression models and, based on the review, select which of the three surgical intervention options is likely to provide the patient with the best long-term outcome. Of course, selecting the optimal intervention can also be fully or semi-automated, as described herein.

Based off of the modeled disease progression, the systems and methods described herein can also (i) identify the optimal time for surgical intervention, and/or (ii) identify the optimal type of surgical procedure for the patient. In some embodiments, the present technology therefore includes an intervention timing module that includes an algorithm, machine learning model, or other software analytical tool for determining the optimal time for surgical intervention in a particular patient. This can be done, for example, by analyzing patient reference data that includes (i) pre-operative disease progression metrics for individual reference patients, (ii) disease metrics at the time of surgical intervention for individual reference patients, (iii) post-operative disease progression metrics for individual reference patients, and/or (iv) scored surgical outcomes for individual reference patients. The intervention timing module can compare the disease metrics for a particular patient to the reference patient data sets to determine, for similar patients, the point of disease progression at which surgical intervention produced the most favorable outcomes.

As a non-limiting example, the reference patient data sets may include data associated with reference patients' sagittal vertical axis. The data can include (i) sagittal vertical axis values for individual patients over a period of time before surgical intervention (e.g., how fast and to what degree the sagittal vertical axis value changed), (ii) sagittal vertical axis of the individual patients at the time of surgical intervention, (iii) the change in sagittal vertical axis after surgical intervention, and (iv) the degree to which the surgical intervention was successful (e.g., based on pain, quality of life, or other factors). Based on the foregoing data, the intervention timing module can, based on a particular patient's sagittal vertical axis value, identify at which point surgical intervention will have the highest likelihood of producing the most favorable outcome. Of course, the foregoing metric is provided by way of example only, and the intervention timing module can incorporate other metrics (e.g., lumbar lordosis, pelvic tilt, sagittal vertical axis, cobb angel, coronal offset, disability scores, functional ability scores, flexibility scores, VAS pain scores) instead of or in combination with sagittal vertical axis to predict the time at which surgical intervention has the highest probability of providing a favorable outcome for the particular patient.

The intervention timing module may also incorporate one or more mathematical rules based on value thresholds for various disease metrics. For example, the intervention timing module may indicate surgical intervention is necessary if one or more disease metrics exceed a predetermined threshold or meet some other criteria. Representative thresholds that indicate surgical intervention may be necessary include SVA values greater than 7 mm, a mismatch between lumbar lordosis and pelvic incidence greater than 10 degrees, a cobb angle of greater than 10 degrees, and/or a combination of cobb angle and LL/PI mismatch greater than 20 degrees. Of course, other threshold values and metrics can be used; the foregoing are provided as examples only and in no way limit the present disclosure. In some embodiments, the foregoing rules can be tailored to specific patient populations (e.g., for males over 50 years of age, an SVA value greater than 7 mm indicates the need for surgical intervention). If a particular patient does not exceed the thresholds indicating surgical intervention is recommended, the intervention timing module may provide an estimate for when the patient's metrics will exceed one or more thresholds, thereby providing the patient with an estimate of when surgical intervention may become recommended.

The present technology may also include a treatment planning module that can identify the optimal type of surgical procedure for the patient based on the disease progression of the patient. The treatment planning module can be an algorithm, machine learning model, or other software analytical tool trained or otherwise based on a plurality of reference patient data sets, as previously described. The treatment planning module may also incorporate one or more mathematical rules for identifying surgical procedures. As a non-limiting example, if a LL/PI mismatch is between 10 and 20 degrees, the treatment planning module may recommend an anterior fusion surgery, but if the LL/PI mismatch is greater than 20 degrees, the treatment planning module may recommend both anterior and posterior fusion surgery. As another non-limiting example, if a SVA value is between 7 mm and 15 mm, the treatment planning module may recommend posterior fusion surgery, but if the SVA is above 15 mm, the treatment planning module may recommend both posterior fusion surgery and anterior fusion surgery. Of course, other rules can be used; the foregoing are provided as examples only and in no way limit the present disclosure.

Without being bound by theory, incorporating disease progression modeling into the patient-specific medical procedures described herein may even further increase the effectiveness of the procedures. For example, in many cases it may be disadvantageous operate after a patient's disease progresses to an irreversible or unstable state. However, it may also be disadvantageous to operate too early, before the patient's disease is causing symptoms and/or if the patient's disease may not progress further. The disease progression module and/or the intervention timing module can therefore help identify the window of time during which surgical intervention in a particular patient has the highest probability of providing a favorable outcome for the patient.

As one skilled in the art will appreciate, any of the software modules described previously may be combined into a single software module for performing the operations described herein. Likewise, the software modules can be distributed across any combination of the computing systems and devices described herein, and are not limited to the express arrangements described herein. Accordingly, any of the operations described herein can be performed by any of the computing devices or systems described herein, unless expressly noted otherwise.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In some embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality, and any two components capable of being so associated can also be viewed as being "operably couplable" to each other to achieve the desired functionality. Specific examples of operably couplable include but are not limited to physically mateable and/or physically interacting components and/or wirelessly interactable and/or wirelessly interacting components and/or logically interacting and/or logically interactable components.

The embodiments, features, systems, devices, materials, methods and techniques described herein may, in some embodiments, be similar to any one or more of the embodiments, features, systems, devices, materials, methods and techniques described in the following:

U.S. application Ser. No. 16/048,167, filed on Jul. 27, 2017, titled "SYSTEMS AND METHODS FOR ASSISTING AND AUGMENTING SURGICAL PROCEDURES;"

U.S. application Ser. No. 16/242,877, filed on Jan. 8, 2019, titled "SYSTEMS AND METHODS OF ASSISTING A SURGEON WITH SCREW PLACEMENT DURING SPINAL SURGERY;"

U.S. application Ser. No. 16/207,116, filed on Dec. 1, 2018, titled "SYSTEMS AND METHODS FOR MULTI-PLANAR ORTHOPEDIC ALIGNMENT;"

U.S. application Ser. No. 16/352,699, filed on Mar. 13, 2019, titled "SYSTEMS AND METHODS FOR ORTHOPEDIC IMPLANT FIXATION;"

U.S. application Ser. No. 16/383,215, filed on Apr. 12, 2019, titled "SYSTEMS AND METHODS FOR ORTHOPEDIC IMPLANT FIXATION;"

U.S. application Ser. No. 16/569,494, filed on Sep. 12, 2019, titled "SYSTEMS AND METHODS FOR ORTHOPEDIC IMPLANTS;" and U.S. Application No. 62/773,127, filed on Nov. 29, 2018, titled "SYSTEMS AND METHODS FOR ORTHOPEDIC IMPLANTS."

U.S. Application No. 62/928,909, filed on Oct. 31, 2019, titled "SYSTEMS AND METHODS FOR DESIGNING ORTHOPEDIC IMPLANTS BASED ON TISSUE CHARACTERISTICS;"

U.S. application Ser. No. 16/735,222 (now U.S. Pat. No. 10,902,944), filed Jan. 6, 2020, titled "PATIENT-SPECIFIC MEDICAL PROCEDURES AND DEVICES, AND ASSOCIATED SYSTEMS AND METHODS;"

U.S. application Ser. No. 16/987,113, filed Aug. 6, 2020, titled "PATIENT-SPECIFIC ARTIFICIAL DISCS, IMPLANTS AND ASSOCIATED SYSTEMS AND METHODS;"

U.S. application Ser. No. 16/990,810, filed Aug. 11, 2020, titled "LINKING PATIENT-SPECIFIC MEDICAL DEVICES WITH PATIENT-SPECIFIC DATA, AND ASSOCIATED SYSTEMS, DEVICES, AND METHODS;"

U.S. application Ser. No. 17/085,564, filed Oct. 30, 2020, titled "SYSTEMS AND METHODS FOR DESIGNING ORTHOPEDIC IMPLANTS BASED ON TISSUE CHARACTERISTICS;"

U.S. application Ser. No. 17/100,396, filed Nov. 20, 2020, titled "PATIENT-SPECIFIC VERTEBRAL IMPLANTS WITH POSITIONING FEATURES;"

U.S. application Ser. No. 17/124,822, filed Dec. 17, 2020, titled "PATIENT-SPECIFIC MEDICAL PROCEDURES AND DEVICES, AND ASSOCIATED SYSTEMS AND METHODS;" and International Application No. PCT/US2021/012065, filed Jan. 4, 2021, titled "PATIENT-SPECIFIC MEDICAL PROCEDURES AND DEVICES, AND ASSOCIATED SYSTEMS AND METHODS."

All of the above-identified patents and applications are incorporated by reference in their entireties. In addition, the embodiments, features, systems, devices, materials, methods and techniques described herein may, in certain embodiments, be applied to or used in connection with any one or more of the embodiments, features, systems, devices, or other matter.

The ranges disclosed herein also encompass any and all overlap, sub-ranges, and combinations thereof. Language such as "up to," "at least," "greater than," "less than," "between," or the like includes the number recited. Numbers preceded by a term such as "approximately," "about," and "substantially" as used herein include the recited numbers (e.g., about 10%=10%), and also represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of the stated amount.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

What is claimed is:

1. A computer-implemented method, comprising:
    performing a digital surgical simulation for each of a plurality of candidate patient-specific surgical interventions that each provide a corresponding patient-specific anatomical correction, the digital surgical simulations each including a corresponding predictive model of patient anatomy for a particular time after the corresponding candidate patient-specific interventions, wherein the digital surgical simulations are performed at least in part by at least one trained machine learning module trained using reference patient data;
    displaying surgical simulation data from at least one of the digital surgical simulations, wherein the surgical simulation data includes the corresponding predictive model of patient anatomy for user review;
    receiving a selection of one of the plurality of candidate patient-specific surgical interventions; and
    designing one or more patient-specific implants based on the selected candidate patient-specific surgical intervention, wherein the one or more patient-specific implants are configured to achieve a patient-specific anatomical correction associated with the selected candidate patient-specific surgical intervention when implanted in a patient with the patient anatomy.

2. The computer-implemented method of claim 1, wherein one or more of the predictive models incorporate anticipated post-operative disease progression.

3. The computer-implemented method of claim 1, wherein the particular time is less than or equal to 2 years post-surgery.

4. The computer-implemented method of claim 1, wherein the particular time is between 1 year and 5 years post-surgery.

5. The computer-implemented method of claim 1, further comprising performing a digital simulation of changes in the patient anatomy if no surgical intervention were to occur.

6. The computer-implemented method of claim 1, further comprising:
    determining a rate of disease progression for the patient;
    simulating disease progression of a corrected anatomical configuration of the patient achieved by the one or more patient-specific implants based on the rate of disease progression; and
    generating viewable disease progression data representing the simulated disease progression.

7. The computer-implemented method of claim 6, further comprising:
    receiving first user input associated with one or more viewable virtual simulations of the disease progression;
    generating one or more modified viewable virtual simulations based on the received user input; and
    receiving second user input for the patient-specific anatomical correction that is based on at least one of the one or more modified viewable virtual simulations.

8. The computer-implemented method of claim 6, further comprising:
    designing at least a portion of the one or more patient-specific implants based on one or more viewable virtual simulations of predicted disease progression in the patient.

9. The computer-implemented method of claim 1, further comprising generating one or more viewable virtual simulations representing predicted disease progression over the particular time.

10. The computer-implemented method of claim 1, further comprising:
    determining a fixed rate of disease progression for the patient; and
    simulating disease progression of a corrected anatomical configuration of the patient based on the fixed rate of disease progression.

11. The computer-implemented method of claim 1, further comprising:
    determining a variable rate of disease progression for the patient; and
    simulating disease progression of the corrected anatomical configuration based on the variable rate of disease progression.

12. The computer-implemented method of claim 1, further comprising:
    generating a surgical plan for achieving the patient-specific anatomical correction, wherein the surgical plan includes planned post-operative spinal alignment information.

13. A computer-implemented method, comprising:
    performing a plurality of digital surgical simulations associated with a patient-specific surgery;
    generating a planned post-operative virtual anatomical model representing a corrected anatomical configuration of a patient based on at least one of the plurality of digital surgical simulations;
    using at least one-trained machine-learning module to determine predicted corrected anatomical data of the patient after a post-operative period of time, wherein the at least one-trained machine-learning module is trained using reference patient data, and wherein the predicted corrected anatomical data of the patient is viewable by a user to plan a surgical procedure for the patient; and
    designing one or more patient-specific implants configured to achieve the corrected anatomical configuration when implanted in the patient.

14. The computer-implemented method of claim 13, wherein the predictive models incorporate anticipated post-operative disease progression.

15. The computer-implemented method of claim 13, wherein the post-operative period of time is less than 2 years post-surgery.

16. The computer-implemented method of claim 13, wherein the post-operative period of time is between 1 year and 5 years post-surgery.

17. The computer-implemented method of claim 13, further comprising performing a digital simulation of changes in patient anatomy if no surgical intervention were to occur.

18. The computer-implemented method of claim 13, further comprising:
determining a rate of disease progression for the patient;
simulating disease progression of the corrected anatomical configuration based on the rate of disease progression; and
generating viewable disease progression data representing the simulated disease progression.

19. The computer-implemented method of claim 13, further comprising:
receiving user input associated with one or more viewable virtual simulations of the disease progression;
generating one or more modified viewable virtual simulations based on the received user input;
selecting the corrected anatomical configuration for the patient based on at least one of the one or more modified viewable virtual simulations; and
designing at least a portion of the one or more patient-specific implants based on the one or more viewable virtual simulations.

20. The computer-implemented method of claim 13, further comprising:
determining a fixed rate of disease progression for the patient; and
simulating disease progression of the corrected anatomical configuration based on the fixed rate of disease progression, wherein the predicted corrected anatomical data is associated with the simulating of the disease progression.

21. The computer-implemented method of claim 13, further comprising:
determining a variable rate of disease progression for the patient; and
simulating disease progression of the corrected anatomical configuration based on the variable rate of disease progression, wherein the predicted corrected anatomical data is associated with the simulating of the disease progression.

22. The computer-implemented method of claim 13, wherein the predicted corrected anatomical data includes patient-specific spinal corrections that compensate for predicted disease progression of a spine of the patient.

23. The computer-implemented method of claim 13, wherein the predicted corrected spinal data includes data of positional relationships between anatomic elements of the patient's spine affected by disease progression.

24. The computer-implemented method of claim 13, wherein the predicted corrected anatomical data represents spinal alignment of the patient after the post-operative period and includes at least one of a predicted coronal parameter, a predicted sagittal parameter, a predicted pelvic incidence angle, a predicted Cobb angle, a predicted lordosis angle, or a predicted intervertebral space height.

25. The computer-implemented method of claim 13, wherein the planned post-operative virtual anatomical model is based on one or more reference patient data sets.

26. The computer-implemented method of claim 13, further comprising predicting anatomical compensation associated with disease progression of the patient.

27. A system comprising:
one or more processors; and
one or more memories storing instructions that, when executed by the one or more processors, cause the system to perform a process comprising:
performing a digital surgical simulation for each of a plurality of candidate patient-specific surgical interventions that each provide a corresponding patient-specific anatomical correction, the digital surgical simulations each including a corresponding predictive model of patient anatomy for a particular time after the corresponding candidate patient-specific interventions, wherein the digital surgical simulations are performed at least in part by at least one trained machine learning module trained using reference patient data;
displaying surgical simulation data from at least one of the digital surgical simulations, wherein the surgical simulation data includes the corresponding predictive model of patient anatomy for user review;
receiving a selection of one of the plurality of candidate patient-specific surgical interventions; and
designing one or more patient-specific implants based on the selected candidate patient-specific surgical intervention, wherein the one or more patient-specific implants are configured to achieve a patient-specific anatomical correction associated with the selected candidate patient-specific surgical intervention when implanted in a patient with the patient anatomy.

28. A non-transitory computer-readable medium storing instructions that, when executed by a computing system, cause the computing system to perform operations comprising:
performing a digital surgical simulation for each of a plurality of candidate patient-specific surgical interventions that each provide a corresponding patient-specific anatomical correction, the digital surgical simulations each including a corresponding predictive model of patient anatomy for a particular time after the corresponding candidate patient-specific interventions, wherein the digital surgical simulations are performed at least in part by at least one trained machine learning module trained using reference patient data;
displaying surgical simulation data from at least one of the digital surgical simulations, wherein the surgical simulation data includes the corresponding predictive model of patient anatomy for user review;
receiving a selection of one of the plurality of candidate patient-specific surgical interventions; and
designing one or more patient-specific implants based on the selected candidate patient-specific surgical intervention, wherein the one or more patient-specific implants are configured to achieve a patient-specific anatomical correction associated with the selected candidate patient-specific surgical intervention when implanted in a patient with the patient anatomy.

* * * * *